(12) United States Patent
Moberg et al.

(10) Patent No.: US 9,687,266 B2
(45) Date of Patent: Jun. 27, 2017

(54) METHODS AND DEVICES FOR CUTTING AND ABRADING TISSUE

(75) Inventors: John Robert Moberg, Elk River, MN (US); Alex Yang, San Francisco, CA (US); Christopher B. Brodeur, Plymouth, MN (US); William Joseph Whealon, Chaska, MN (US); Kee Lee, Newark, CA (US); Phyllis Yuen, Fremont, CA (US); Darren Doud, San Jose, CA (US)

(73) Assignee: Covidien LP, Mansfield, MA (US)

( * ) Notice: Subject to any disclaimer, the term of this patent is extended or adjusted under 35 U.S.C. 154(b) by 699 days.

(21) Appl. No.: 12/768,281

(22) Filed: Apr. 27, 2010

(65) Prior Publication Data

US 2010/0312263 A1    Dec. 9, 2010

Related U.S. Application Data

(60) Provisional application No. 61/173,845, filed on Apr. 29, 2009.

(51) Int. Cl.
*A61B 17/22* (2006.01)
*A61B 17/3207* (2006.01)
*A61B 17/32* (2006.01)

(52) U.S. Cl.
CPC ............ *A61B 17/320758* (2013.01); *A61B 17/320783* (2013.01); *A61B 2017/320004* (2013.01); *A61B 2017/320791* (2013.01)

(58) Field of Classification Search
CPC ........ A61B 17/3207; A61B 17/320758; A61B 17/320783; A61B 2017/320791; A61B 2017/320004; A61B 2017/320766

USPC ................. 606/159, 158, 167, 170
See application file for complete search history.

(56) References Cited

U.S. PATENT DOCUMENTS

| 1,481,078 | A | 1/1924 | Albertson |
|---|---|---|---|
| 2,178,790 | A | 11/1939 | Henry |
| 2,701,559 | A | 2/1955 | Cooper |
| 2,850,007 | A | 9/1958 | Lingley |

(Continued)

FOREIGN PATENT DOCUMENTS

| CA | 2000621 | 4/1990 |
|---|---|---|
| DE | 3732236 C1 | 12/1988 |

(Continued)

OTHER PUBLICATIONS

Jul. 19, 2011 Communication in European Application No. 04760155.4 (5 pages).

(Continued)

*Primary Examiner* — Anh Dang

(57) ABSTRACT

The present invention provides an atherectomy catheter which has a cutting element that is able to cut both soft tissue and hard tissue, and methods of cutting material from a blood vessel lumen using a rotating cutting element. The cutting element has a sharp cutting edge that surrounds a cup-shaped surface and at least one surface of abrasive material. The cup-shaped surface directs the cut material into a tissue chamber. The cutting edge and the cup-shaped surface together are well suited to cut and remove relatively soft tissue from the blood vessel. The abrasive material surface in combination with the cutting element is well suited to abrade and remove hard material from the blood vessel.

20 Claims, 16 Drawing Sheets

(56) References Cited

U.S. PATENT DOCUMENTS

| | | |
|---|---|---|
| 3,064,651 A | 11/1960 | Henderson |
| 3,082,805 A | 3/1963 | Royce |
| 3,320,957 A | 5/1967 | Sokolik |
| 3,614,953 A | 10/1971 | Moss |
| 3,683,891 A | 8/1972 | Eskridge et al. |
| 3,705,577 A | 12/1972 | Sierra |
| 3,732,858 A | 5/1973 | Banko |
| 3,749,085 A | 7/1973 | Willson et al. |
| 3,800,783 A | 4/1974 | Jamshidi |
| 3,815,604 A | 6/1974 | O'Malley et al. |
| 3,831,585 A | 8/1974 | Brondy et al. |
| 3,837,345 A | 9/1974 | Matar |
| 3,845,375 A | 10/1974 | Stiebel |
| 3,937,222 A | 2/1976 | Banko |
| 3,945,375 A | 3/1976 | Banko |
| 3,976,077 A | 8/1976 | Kerfoot, Jr. |
| 3,995,619 A | 12/1976 | Glatzer |
| 4,007,732 A | 2/1977 | Kvavle et al. |
| 4,020,847 A | 5/1977 | Clark, III |
| 4,030,503 A | 6/1977 | Clark, III |
| 4,034,744 A | 7/1977 | Goldberg |
| 4,038,985 A | 8/1977 | Chiulli |
| 4,112,708 A | 9/1978 | Fukuda |
| 4,177,797 A | 12/1979 | Baylis et al. |
| 4,210,146 A | 7/1980 | Banko |
| 4,273,128 A | 6/1981 | Lary |
| 4,306,562 A | 12/1981 | Osborne |
| 4,306,570 A | 12/1981 | Matthews |
| 4,349,032 A | 9/1982 | Koyata |
| 4,368,730 A | 1/1983 | Sharrock |
| 4,424,045 A | 1/1984 | Kulischenko et al. |
| 4,436,091 A | 3/1984 | Banko |
| 4,445,509 A | 5/1984 | Auth |
| 4,490,139 A | 12/1984 | Huizenga et al. |
| 4,494,057 A | 1/1985 | Hotta |
| 4,512,344 A | 4/1985 | Barber |
| 4,589,412 A | 5/1986 | Kensey |
| 4,603,694 A | 8/1986 | Wheeler |
| 4,620,547 A | 11/1986 | Boebel |
| 4,631,052 A | 12/1986 | Kensey |
| 4,646,719 A | 3/1987 | Neuman et al. |
| 4,646,736 A | 3/1987 | Auth |
| 4,646,738 A | 3/1987 | Trott |
| 4,649,919 A | 3/1987 | Thimsen et al. |
| 4,653,496 A | 3/1987 | Bundy et al. |
| 4,664,112 A | 5/1987 | Kensey et al. |
| 4,669,469 A | 6/1987 | Gifford, III et al. |
| 4,679,558 A | 7/1987 | Kensey et al. |
| 4,686,982 A | 8/1987 | Nash |
| 4,692,141 A | 9/1987 | Mahurkar |
| 4,696,298 A | 9/1987 | Higgins et al. |
| 4,696,667 A | 9/1987 | Masch |
| 4,705,038 A | 11/1987 | Sjostrom |
| 4,706,671 A | 11/1987 | Weinrib |
| 4,728,319 A | 3/1988 | Masch |
| 4,729,763 A | 3/1988 | Henrie |
| 4,730,616 A | 3/1988 | Frisbie et al. |
| 4,732,154 A | 3/1988 | Shiber |
| 4,733,662 A | 3/1988 | DeSatnick et al. |
| 4,745,919 A | 5/1988 | Bundey et al. |
| 4,747,406 A | 5/1988 | Nash |
| 4,747,821 A | 5/1988 | Kensey et al. |
| 4,749,376 A | 6/1988 | Kensey et al. |
| 4,754,755 A | 7/1988 | Husted |
| 4,757,819 A | 7/1988 | Yokoi et al. |
| 4,765,332 A | 8/1988 | Fischell et al. |
| 4,771,774 A | 9/1988 | Simpson et al. |
| 4,781,186 A | 11/1988 | Simpson et al. |
| 4,784,636 A | 11/1988 | Rydell |
| 4,790,812 A | 12/1988 | Hawkins, Jr. et al. |
| 4,794,931 A | 1/1989 | Yock |
| 4,817,613 A | 4/1989 | Jaraczewski et al. |
| 4,819,634 A | 4/1989 | Shiber |
| 4,819,635 A | 4/1989 | Shapiro |
| 4,838,268 A | 6/1989 | Keith et al. |
| 4,842,579 A | 6/1989 | Shiber |
| 4,844,064 A | 7/1989 | Thimsen et al. |
| 4,848,343 A | 7/1989 | Wallsten et al. |
| 4,850,957 A | 7/1989 | Summers |
| 4,857,046 A | 8/1989 | Stevens et al. |
| 4,867,157 A | 9/1989 | McGurk-Burleson et al. |
| 4,870,953 A | 10/1989 | DonMicheal et al. |
| 4,883,458 A | 11/1989 | Shiber |
| 4,886,061 A | 12/1989 | Fischell et al. |
| 4,886,490 A | 12/1989 | Shiber |
| 4,887,613 A | 12/1989 | Farr et al. |
| 4,894,051 A | 1/1990 | Shiber |
| 4,899,757 A | 2/1990 | Pope, Jr. et al. |
| 4,919,133 A | 4/1990 | Chiang |
| 4,923,462 A | 5/1990 | Stevens |
| 4,926,858 A | 5/1990 | Gifford, III et al. |
| 4,928,693 A | 5/1990 | Goodin et al. |
| 4,936,987 A | 6/1990 | Persinski et al. |
| RE33,258 E | 7/1990 | Onik et al. |
| 4,950,238 A | 8/1990 | Sullivan |
| 4,954,338 A | 9/1990 | Mattox |
| 4,957,482 A | 9/1990 | Shiber |
| 4,966,604 A | 10/1990 | Reiss |
| 4,973,409 A | 11/1990 | Cook |
| 4,979,939 A | 12/1990 | Shiber |
| 4,979,951 A | 12/1990 | Simpson |
| 4,986,807 A | 1/1991 | Farr |
| 4,990,134 A | 2/1991 | Auth |
| 4,994,067 A | 2/1991 | Summers |
| 4,997,435 A | 3/1991 | Demeter |
| 5,000,185 A | 3/1991 | Yock |
| 5,002,553 A | 3/1991 | Shiber |
| 5,003,918 A | 4/1991 | Olson et al. |
| 5,007,896 A | 4/1991 | Shiber |
| 5,009,659 A | 4/1991 | Hamlin et al. |
| 5,019,088 A | 5/1991 | Farr |
| 5,024,234 A | 6/1991 | Leary et al. |
| 5,024,651 A | 6/1991 | Shiber |
| 5,026,384 A | 6/1991 | Farr et al. |
| 5,029,588 A | 7/1991 | Yock et al. |
| 5,030,201 A | 7/1991 | Palestrant |
| 5,047,040 A | 9/1991 | Simpson et al. |
| 5,049,124 A | 9/1991 | Bales, Jr. |
| 5,053,044 A | 10/1991 | Mueller et al. |
| 5,054,492 A | 10/1991 | Scribner et al. |
| 5,064,435 A | 11/1991 | Porter |
| 5,071,425 A | 12/1991 | Gifford et al. |
| 5,074,841 A | 12/1991 | Ademovic et al. |
| 5,077,506 A | 12/1991 | Krause et al. |
| 5,078,722 A | 1/1992 | Stevens |
| 5,084,010 A | 1/1992 | Plaia et al. |
| 5,085,662 A | 2/1992 | Willard |
| 5,087,265 A | 2/1992 | Summers |
| 5,092,839 A | 3/1992 | Kipperman |
| 5,092,873 A | 3/1992 | Simpson et al. |
| 5,095,911 A | 3/1992 | Pomeranz |
| 5,100,423 A | 3/1992 | Fearnot |
| 5,100,424 A | 3/1992 | Jang et al. |
| 5,100,426 A | 3/1992 | Nixon |
| 5,110,822 A | 5/1992 | Sherba et al. |
| 5,112,345 A | 5/1992 | Farr |
| 5,114,399 A | 5/1992 | Kovalcheck |
| 5,115,814 A | 5/1992 | Griffith et al. |
| 5,120,323 A | 6/1992 | Shockey et al. |
| 5,127,902 A | 7/1992 | Fischell |
| 5,127,917 A | 7/1992 | Niederhauser et al. |
| 5,135,531 A | 8/1992 | Shiber |
| 5,154,705 A | 10/1992 | Fleischhacker et al. |
| 5,154,724 A | 10/1992 | Andrews |
| 5,165,421 A | 11/1992 | Fleischhacker et al. |
| 5,176,693 A | 1/1993 | Pannek, Jr. |
| 5,178,625 A | 1/1993 | Groshong |
| 5,181,920 A | 1/1993 | Mueller et al. |
| 5,183,432 A | 2/1993 | Noguchi |
| 5,190,528 A | 3/1993 | Fonger et al. |
| 5,192,291 A | 3/1993 | Pannek, Jr. |
| 5,195,956 A | 3/1993 | Stockmeier |
| 5,211,651 A | 5/1993 | Reger et al. |
| 5,217,474 A | 6/1993 | Zacca et al. |

(56) References Cited

U.S. PATENT DOCUMENTS

| | | |
|---|---|---|
| 5,222,966 A | 6/1993 | Perkins et al. |
| 5,224,488 A | 7/1993 | Neuffer |
| 5,224,945 A | 7/1993 | Pannek, Jr. |
| 5,224,949 A | 7/1993 | Gomringer et al. |
| 5,226,909 A | 7/1993 | Evans et al. |
| 5,226,910 A | 7/1993 | Kajiyama et al. |
| 5,234,451 A | 8/1993 | Osypka |
| 5,242,460 A | 9/1993 | Klein et al. |
| 5,242,461 A | 9/1993 | Kortenbach et al. |
| 5,250,059 A | 10/1993 | Andreas et al. |
| 5,250,065 A | 10/1993 | Clement et al. |
| 5,263,928 A | 11/1993 | Trauthen et al. |
| 5,263,959 A | 11/1993 | Fischell |
| 5,267,955 A | 12/1993 | Hanson |
| 5,267,982 A | 12/1993 | Sylvanowicz |
| 5,269,793 A | 12/1993 | Simpson et al. |
| 5,273,526 A | 12/1993 | Dance et al. |
| 5,282,484 A | 2/1994 | Reger |
| 5,284,486 A | 2/1994 | Kotula et al. |
| 5,285,795 A | 2/1994 | Ryan et al. |
| 5,295,493 A | 3/1994 | Radisch, Jr. |
| 5,300,085 A | 4/1994 | Yock |
| 5,306,294 A | 4/1994 | Winston et al. |
| 5,308,354 A | 5/1994 | Zacca et al. |
| 5,312,425 A | 5/1994 | Evans et al. |
| 5,312,427 A | 5/1994 | Shturman |
| 5,314,438 A | 5/1994 | Shturman |
| 5,318,032 A | 6/1994 | Lonsbury et al. |
| 5,318,528 A | 6/1994 | Heaven et al. |
| 5,318,576 A | 6/1994 | Plassche, Jr. et al. |
| 5,321,501 A | 6/1994 | Swanson et al. |
| 5,322,508 A | 6/1994 | Viera |
| 5,350,390 A | 9/1994 | Sher |
| 5,356,418 A | 10/1994 | Shturman |
| 5,358,472 A | 10/1994 | Vance et al. |
| 5,358,485 A | 10/1994 | Vance et al. |
| 5,360,432 A | 11/1994 | Shturman |
| 5,366,463 A | 11/1994 | Ryan |
| 5,368,035 A | 11/1994 | Hamm et al. |
| 5,370,609 A | 12/1994 | Drasler et al. |
| 5,370,651 A | 12/1994 | Summers |
| 5,372,601 A | 12/1994 | Lary |
| 5,372,602 A | 12/1994 | Burke |
| 5,373,619 A | 12/1994 | Fleischhacker et al. |
| 5,373,849 A | 12/1994 | Maroney et al. |
| 5,377,682 A | 1/1995 | Ueno et al. |
| 5,378,234 A | 1/1995 | Hammerslag et al. |
| 5,383,460 A | 1/1995 | Jang et al. |
| 5,395,311 A | 3/1995 | Andrews |
| 5,395,313 A | 3/1995 | Naves et al. |
| 5,395,335 A | 3/1995 | Jang |
| 5,397,345 A | 3/1995 | Lazarus |
| 5,402,790 A | 4/1995 | Jang et al. |
| 5,403,334 A | 4/1995 | Evans et al. |
| 5,409,454 A | 4/1995 | Fischell et al. |
| 5,413,107 A | 5/1995 | Oakley et al. |
| 5,419,774 A | 5/1995 | Willard et al. |
| 5,423,740 A | 6/1995 | Sullivan |
| 5,423,799 A | 6/1995 | Shiu |
| 5,423,838 A | 6/1995 | Willard |
| 5,423,846 A | 6/1995 | Fischell |
| 5,427,107 A | 6/1995 | Milo et al. |
| 5,429,136 A | 7/1995 | Milo et al. |
| 5,431,673 A | 7/1995 | Summers et al. |
| 5,441,510 A | 8/1995 | Simpson et al. |
| 5,443,446 A | 8/1995 | Shturman |
| 5,443,497 A | 8/1995 | Venbrux |
| 5,444,078 A | 8/1995 | Yu et al. |
| 5,445,155 A | 8/1995 | Sieben |
| 5,449,369 A | 9/1995 | Imran |
| 5,451,233 A | 9/1995 | Yock |
| 5,454,809 A | 10/1995 | Janssen |
| 5,456,667 A | 10/1995 | Ham et al. |
| 5,456,689 A | 10/1995 | Kresch et al. |
| 5,458,585 A | 10/1995 | Salmon et al. |
| 5,459,570 A | 10/1995 | Swanson et al. |
| 5,464,016 A | 11/1995 | Nicholas et al. |
| 5,470,415 A | 11/1995 | Perkins et al. |
| 5,485,042 A | 1/1996 | Burke et al. |
| 5,485,840 A | 1/1996 | Bauman |
| 5,487,729 A | 1/1996 | Avellanet et al. |
| 5,489,295 A | 2/1996 | Piplani et al. |
| 5,491,524 A | 2/1996 | Hellmuth et al. |
| 5,496,267 A | 3/1996 | Drasler et al. |
| 5,501,694 A | 3/1996 | Ressemann et al. |
| 5,503,155 A | 4/1996 | Salmon et al. |
| 5,505,210 A | 4/1996 | Clement |
| 5,507,292 A | 4/1996 | Jang et al. |
| 5,507,760 A | 4/1996 | Wynne et al. |
| 5,507,761 A | 4/1996 | Duer |
| 5,507,795 A | 4/1996 | Chiang et al. |
| 5,512,044 A | 4/1996 | Duer |
| 5,514,115 A | 5/1996 | Frantzen et al. |
| 5,520,189 A | 5/1996 | Malinowski et al. |
| 5,522,825 A | 6/1996 | Kropf et al. |
| 5,522,880 A | 6/1996 | Barone et al. |
| 5,527,292 A | 6/1996 | Adams et al. |
| 5,527,298 A | 6/1996 | Vance et al. |
| 5,527,325 A | 6/1996 | Conley et al. |
| 5,531,685 A | 7/1996 | Hemmer et al. |
| 5,531,690 A | 7/1996 | Solar |
| 5,531,700 A | 7/1996 | Moore et al. |
| 5,540,707 A | 7/1996 | Ressemann et al. |
| 5,549,601 A | 8/1996 | McIntyre et al. |
| 5,554,163 A | 9/1996 | Shturman |
| 5,556,408 A | 9/1996 | Farhat |
| 5,558,093 A | 9/1996 | Pomeranz |
| 5,562,726 A | 10/1996 | Chuter |
| 5,562,728 A | 10/1996 | Lazarus et al. |
| 5,569,275 A | 10/1996 | Kotula et al. |
| 5,569,276 A | 10/1996 | Jang et al. |
| 5,569,277 A | 10/1996 | Evans et al. |
| 5,569,279 A | 10/1996 | Rainin |
| 5,570,693 A | 11/1996 | Jang et al. |
| 5,571,122 A | 11/1996 | Kelly et al. |
| 5,571,130 A | 11/1996 | Simpson et al. |
| 5,575,817 A | 11/1996 | Martin |
| 5,584,842 A | 12/1996 | Fogarty et al. |
| 5,584,843 A | 12/1996 | Wulfman et al. |
| 5,609,605 A | 3/1997 | Marshall et al. |
| 5,618,293 A | 4/1997 | Sample et al. |
| 5,620,447 A | 4/1997 | Smith et al. |
| 5,624,457 A | 4/1997 | Farley et al. |
| 5,626,562 A | 5/1997 | Castro |
| 5,626,576 A | 5/1997 | Janssen |
| 5,628,761 A | 5/1997 | Rizik |
| 5,632,754 A | 5/1997 | Farley et al. |
| 5,632,755 A | 5/1997 | Nordgren et al. |
| 5,634,464 A | 6/1997 | Jang et al. |
| 5,643,296 A | 7/1997 | Hundertmark et al. |
| 5,643,298 A | 7/1997 | Nordgren et al. |
| 5,649,941 A | 7/1997 | Lary |
| 5,660,180 A | 8/1997 | Malinowski et al. |
| 5,662,671 A | 9/1997 | Barbut et al. |
| 5,665,098 A | 9/1997 | Kelly et al. |
| 5,669,920 A | 9/1997 | Conley et al. |
| 5,674,232 A | 10/1997 | Halliburton |
| 5,676,696 A | 10/1997 | Marcade |
| 5,676,697 A | 10/1997 | McDonald |
| 5,681,336 A | 10/1997 | Clement et al. |
| 5,682,897 A | 11/1997 | Pomeranz |
| 5,683,449 A | 11/1997 | Marcade |
| 5,683,453 A | 11/1997 | Palmaz |
| 5,688,234 A | 11/1997 | Frisbie |
| 5,695,506 A | 12/1997 | Pike |
| 5,695,507 A | 12/1997 | Auth et al. |
| 5,697,944 A | 12/1997 | Lary |
| 5,700,240 A | 12/1997 | Barwick, Jr. et al. |
| 5,700,687 A | 12/1997 | Finn |
| 5,707,350 A | 1/1998 | Krause et al. |
| 5,707,376 A | 1/1998 | Kavteladze et al. |
| 5,707,383 A | 1/1998 | Bays et al. |
| 5,709,698 A | 1/1998 | Adams et al. |
| 5,713,913 A | 2/1998 | Lary et al. |

(56) References Cited

U.S. PATENT DOCUMENTS

| | | |
|---|---|---|
| 5,715,825 A | 2/1998 | Crowley |
| 5,716,410 A | 2/1998 | Wang et al. |
| 5,720,735 A | 2/1998 | Dorros |
| 5,724,977 A | 3/1998 | Yock et al. |
| 5,728,123 A | 3/1998 | Lemelson et al. |
| 5,733,296 A | 3/1998 | Rogers et al. |
| 5,735,816 A | 4/1998 | Lieber et al. |
| 5,741,270 A | 4/1998 | Hansen et al. |
| 5,766,192 A | 6/1998 | Zacca |
| 5,772,674 A | 6/1998 | Nakhjavan |
| 5,775,327 A | 7/1998 | Randolph et al. |
| 5,776,114 A | 7/1998 | Frantzen et al. |
| 5,776,153 A | 7/1998 | Rees |
| 5,779,643 A | 7/1998 | Lum et al. |
| 5,779,673 A | 7/1998 | Roth et al. |
| 5,779,721 A | 7/1998 | Nash |
| 5,779,722 A | 7/1998 | Shturman et al. |
| 5,792,157 A | 8/1998 | Mische et al. |
| 5,797,949 A | 8/1998 | Parodi |
| 5,799,655 A | 9/1998 | Jang et al. |
| 5,807,329 A | 9/1998 | Gelman |
| 5,810,867 A | 9/1998 | Zarbatany et al. |
| 5,816,923 A | 10/1998 | Milo et al. |
| 5,820,592 A | 10/1998 | Hammerslag |
| 5,823,971 A | 10/1998 | Robinson et al. |
| 5,824,039 A | 10/1998 | Piplani et al. |
| 5,824,055 A | 10/1998 | Spiridigliozzi et al. |
| 5,827,201 A | 10/1998 | Samson et al. |
| 5,827,229 A | 10/1998 | Auth et al. |
| 5,827,304 A | 10/1998 | Hart |
| 5,827,322 A | 10/1998 | Williams |
| 5,830,224 A | 11/1998 | Cohn et al. |
| 5,836,957 A | 11/1998 | Schulz et al. |
| 5,843,022 A | 12/1998 | Willard et al. |
| 5,843,103 A | 12/1998 | Wulfman |
| 5,843,161 A | 12/1998 | Solovay |
| 5,855,563 A | 1/1999 | Kaplan et al. |
| 5,865,178 A * | 2/1999 | Yock .............................. 600/439 |
| 5,865,748 A | 2/1999 | Co et al. |
| 5,868,685 A | 2/1999 | Powell et al. |
| 5,868,767 A | 2/1999 | Farley et al. |
| 5,871,536 A | 2/1999 | Lazarus |
| 5,873,882 A | 2/1999 | Straub et al. |
| 5,876,414 A | 3/1999 | Straub |
| 5,879,397 A | 3/1999 | Kalberer et al. |
| 5,883,458 A | 3/1999 | Sumita et al. |
| 5,888,201 A | 3/1999 | Stinson et al. |
| 5,895,399 A | 4/1999 | Barbut et al. |
| 5,895,402 A | 4/1999 | Hundertmark et al. |
| 5,902,245 A | 5/1999 | Yock |
| 5,910,150 A | 6/1999 | Saadat |
| 5,911,734 A | 6/1999 | Tsugita et al. |
| 5,916,210 A | 6/1999 | Winston |
| 5,922,003 A | 7/1999 | Anctil et al. |
| 5,935,108 A | 8/1999 | Katoh et al. |
| 5,938,645 A | 8/1999 | Gordon |
| 5,938,671 A | 8/1999 | Katoh et al. |
| 5,938,672 A | 8/1999 | Nash |
| 5,941,869 A | 8/1999 | Patterson et al. |
| 5,947,985 A | 9/1999 | Imran |
| 5,948,184 A | 9/1999 | Frantzen et al. |
| 5,951,480 A | 9/1999 | White et al. |
| 5,951,482 A | 9/1999 | Winston et al. |
| 5,954,745 A | 9/1999 | Gertler et al. |
| 5,968,064 A | 10/1999 | Selmon et al. |
| 5,972,019 A | 10/1999 | Engelson et al. |
| 5,985,397 A | 11/1999 | Witt et al. |
| 5,989,281 A | 11/1999 | Barbut et al. |
| 5,997,557 A | 12/1999 | Barbut et al. |
| 6,001,112 A | 12/1999 | Taylor |
| 6,010,449 A | 1/2000 | Selmon et al. |
| 6,010,522 A | 1/2000 | Barbut et al. |
| 6,013,072 A | 1/2000 | Winston et al. |
| 6,019,778 A | 2/2000 | Wilson et al. |
| 6,022,362 A | 2/2000 | Lee et al. |
| 6,027,450 A | 2/2000 | Brown et al. |
| 6,027,460 A | 2/2000 | Shturman |
| 6,027,514 A | 2/2000 | Stine et al. |
| 6,032,673 A | 3/2000 | Savage et al. |
| 6,036,646 A | 3/2000 | Barthe et al. |
| 6,036,656 A | 3/2000 | Slater |
| 6,036,707 A | 3/2000 | Spaulding |
| 6,048,349 A | 4/2000 | Winston et al. |
| 6,050,949 A | 4/2000 | White et al. |
| 6,063,093 A | 5/2000 | Winston et al. |
| 6,066,153 A | 5/2000 | Lev |
| 6,068,603 A | 5/2000 | Suzuki |
| 6,068,638 A | 5/2000 | Makower |
| 6,081,738 A | 6/2000 | Hinohara et al. |
| RE36,764 E * | 7/2000 | Zacca et al. .................. 606/159 |
| 6,095,990 A | 8/2000 | Parodi |
| 6,099,542 A | 8/2000 | Cohn et al. |
| 6,106,515 A | 8/2000 | Winston et al. |
| 6,110,121 A | 8/2000 | Lenker |
| 6,120,515 A | 9/2000 | Rogers et al. |
| 6,120,516 A | 9/2000 | Selmon et al. |
| 6,126,649 A | 10/2000 | VanTassel et al. |
| 6,129,734 A | 10/2000 | Shturman et al. |
| 6,134,003 A | 10/2000 | Tearney et al. |
| 6,152,909 A | 11/2000 | Bagaoisan et al. |
| 6,152,938 A | 11/2000 | Curry |
| 6,156,046 A | 12/2000 | Passafaro et al. |
| 6,157,852 A | 12/2000 | Selmon et al. |
| 6,159,195 A | 12/2000 | Ha et al. |
| 6,159,225 A | 12/2000 | Makower |
| 6,165,127 A | 12/2000 | Crowley |
| 6,179,859 B1 | 1/2001 | Bates et al. |
| 6,183,432 B1 | 2/2001 | Milo |
| 6,187,025 B1 | 2/2001 | Machek |
| 6,190,353 B1 | 2/2001 | Makower et al. |
| 6,191,862 B1 | 2/2001 | Swanson et al. |
| 6,193,676 B1 | 2/2001 | Winston et al. |
| 6,196,963 B1 | 3/2001 | Williams |
| 6,206,898 B1 | 3/2001 | Honeycutt et al. |
| 6,217,527 B1 | 4/2001 | Selmon et al. |
| 6,217,549 B1 | 4/2001 | Selmon et al. |
| 6,217,595 B1 | 4/2001 | Shturman et al. |
| 6,221,049 B1 | 4/2001 | Selmon et al. |
| 6,221,332 B1 | 4/2001 | Thumm et al. |
| 6,228,049 B1 | 5/2001 | Schroeder et al. |
| 6,228,076 B1 | 5/2001 | Winston et al. |
| 6,231,546 B1 | 5/2001 | Milo et al. |
| 6,231,549 B1 | 5/2001 | Noecker et al. |
| 6,235,000 B1 | 5/2001 | Milo et al. |
| 6,238,405 B1 | 5/2001 | Findlay, III et al. |
| 6,241,667 B1 | 6/2001 | Vetter et al. |
| 6,241,744 B1 | 6/2001 | Imran et al. |
| 6,245,012 B1 | 6/2001 | Kleshinski |
| 6,258,052 B1 | 7/2001 | Milo |
| 6,263,236 B1 | 7/2001 | Kasinkas et al. |
| 6,264,611 B1 | 7/2001 | Ishikawa et al. |
| 6,266,550 B1 | 7/2001 | Selmon et al. |
| 6,277,138 B1 | 8/2001 | Levinson et al. |
| 6,283,951 B1 | 9/2001 | Flaherty et al. |
| 6,283,983 B1 | 9/2001 | Makower et al. |
| 6,299,622 B1 | 10/2001 | Snow et al. |
| 6,299,623 B1 | 10/2001 | Wulfman |
| 6,302,875 B1 | 10/2001 | Makower et al. |
| 6,305,834 B1 | 10/2001 | Schubert et al. |
| 6,312,444 B1 | 11/2001 | Barbut |
| 6,319,242 B1 | 11/2001 | Patterson et al. |
| 6,319,275 B1 | 11/2001 | Lashinski et al. |
| 6,330,884 B1 | 12/2001 | Kim |
| 6,355,005 B1 | 3/2002 | Powell et al. |
| 6,361,545 B1 | 3/2002 | Macoviak et al. |
| 6,375,615 B1 | 4/2002 | Flaherty et al. |
| 6,383,195 B1 | 5/2002 | Richard |
| 6,383,205 B1 | 5/2002 | Samson et al. |
| 6,394,976 B1 | 5/2002 | Winston et al. |
| 6,398,798 B2 | 6/2002 | Selmon et al. |
| 6,422,736 B1 | 7/2002 | Antoniades et al. |
| 6,423,081 B1 | 7/2002 | Lee et al. |
| 6,425,870 B1 | 7/2002 | Flesch |
| 6,428,551 B1 | 8/2002 | Hall et al. |

(56) References Cited

U.S. PATENT DOCUMENTS

| | | |
|---|---|---|
| 6,428,552 B1 | 8/2002 | Sparks |
| 6,443,966 B1 | 9/2002 | Shiu |
| 6,445,939 B1 | 9/2002 | Swanson et al. |
| 6,447,525 B2 | 9/2002 | Follmer et al. |
| 6,451,036 B1 | 9/2002 | Heitzmann et al. |
| 6,454,779 B1 | 9/2002 | Taylor |
| 6,475,226 B1 | 11/2002 | Belef et al. |
| 6,482,217 B1 | 11/2002 | Pintor et al. |
| 6,497,711 B1 | 12/2002 | Plaia et al. |
| 6,501,551 B1 | 12/2002 | Tearney et al. |
| 6,520,975 B2 | 2/2003 | Branco |
| RE38,018 E | 3/2003 | Anctil et al. |
| 6,532,380 B1 | 3/2003 | Close et al. |
| 6,533,749 B1 | 3/2003 | Mitusina et al. |
| 6,561,998 B1 | 5/2003 | Roth et al. |
| 6,565,588 B1 | 5/2003 | Clement et al. |
| 6,569,177 B1 | 5/2003 | Dillard et al. |
| 6,592,526 B1 | 7/2003 | Lenker |
| 6,620,180 B1 | 9/2003 | Bays et al. |
| 6,623,437 B2 | 9/2003 | Hinchliffe et al. |
| 6,623,495 B2 | 9/2003 | Findlay, III et al. |
| 6,623,496 B2 | 9/2003 | Snow et al. |
| 6,629,953 B1 | 10/2003 | Boyd |
| 6,638,233 B2 | 10/2003 | Corvi et al. |
| RE38,335 E | 11/2003 | Aust et al. |
| 6,652,505 B1 | 11/2003 | Tsugita |
| 6,652,548 B2 | 11/2003 | Evans et al. |
| 6,656,195 B2 | 12/2003 | Peters et al. |
| 6,666,874 B2 | 12/2003 | Heitzmann et al. |
| 6,682,543 B2 | 1/2004 | Barbut et al. |
| 6,733,511 B2 | 5/2004 | Hall et al. |
| 6,740,103 B2 | 5/2004 | Hall et al. |
| 6,746,462 B1 | 6/2004 | Selmon et al. |
| 6,764,495 B2 | 7/2004 | Lee et al. |
| 6,790,204 B2 | 9/2004 | Zadno-Azizi et al. |
| 6,790,215 B2 | 9/2004 | Findlay, III et al. |
| 6,818,001 B2 | 11/2004 | Wulfman et al. |
| 6,830,577 B2 | 12/2004 | Nash et al. |
| 6,843,797 B2 | 1/2005 | Nash et al. |
| 6,849,068 B1 | 2/2005 | Bagaoisan et al. |
| 6,863,676 B2 | 3/2005 | Lee et al. |
| 6,911,026 B1 | 6/2005 | Hall et al. |
| 6,970,732 B2 | 11/2005 | Winston et al. |
| 6,997,934 B2 | 2/2006 | Snow et al. |
| 7,153,315 B2 | 12/2006 | Miller |
| 7,172,610 B2 | 2/2007 | Heitzmann et al. |
| 7,208,511 B2 | 4/2007 | Williams et al. |
| 7,235,088 B2 | 6/2007 | Pintor et al. |
| 7,318,831 B2 | 1/2008 | Alvarez et al. |
| 7,388,495 B2 | 6/2008 | Fallin et al. |
| 7,479,148 B2 | 1/2009 | Beaupre |
| 7,488,322 B2 | 2/2009 | Brunnett et al. |
| 7,524,289 B2 | 4/2009 | Lenker |
| 7,603,166 B2 | 10/2009 | Casscells, III et al. |
| 7,708,749 B2 | 5/2010 | Simpson et al. |
| 7,713,235 B2 | 5/2010 | Torrance et al. |
| 7,713,279 B2 | 5/2010 | Simpson et al. |
| 7,729,745 B2 | 6/2010 | Maschke |
| 7,734,332 B2 | 6/2010 | Sher |
| 7,753,852 B2 | 7/2010 | Maschke |
| 7,758,599 B2 | 7/2010 | Snow et al. |
| 7,771,444 B2 | 8/2010 | Patel et al. |
| 7,887,556 B2 | 2/2011 | Simpson et al. |
| 2001/0000041 A1 | 3/2001 | Selmon et al. |
| 2001/0031784 A1 | 10/2001 | Petersen et al. |
| 2001/0031981 A1 | 10/2001 | Evans et al. |
| 2001/0044622 A1 | 11/2001 | Vardi et al. |
| 2001/0049500 A1 | 12/2001 | VanTassel et al. |
| 2002/0019644 A1 | 2/2002 | Hastings et al. |
| 2002/0022788 A1 | 2/2002 | Corvi et al. |
| 2002/0058904 A1 | 5/2002 | Boock et al. |
| 2002/0077373 A1 | 6/2002 | Hudson |
| 2002/0077642 A1 | 6/2002 | Patel et al. |
| 2002/0095141 A1 | 7/2002 | Belef et al. |
| 2002/0103459 A1 | 8/2002 | Sparks et al. |
| 2002/0177800 A1 | 11/2002 | Bagaoisan et al. |
| 2002/0188307 A1 | 12/2002 | Pintor et al. |
| 2003/0018346 A1 | 1/2003 | Follmer et al. |
| 2003/0023263 A1 | 1/2003 | Krolik et al. |
| 2003/0093098 A1 | 5/2003 | Heitzmann et al. |
| 2003/0120295 A1 | 6/2003 | Simpson et al. |
| 2003/0125757 A1 | 7/2003 | Patel et al. |
| 2003/0125758 A1 | 7/2003 | Simpson et al. |
| 2003/0163126 A1 | 8/2003 | West, Jr. |
| 2003/0199747 A1 | 10/2003 | Michlitsch et al. |
| 2003/0206484 A1 | 11/2003 | Childers et al. |
| 2003/0229369 A1 | 12/2003 | Findlay, III et al. |
| 2004/0006358 A1 | 1/2004 | Wulfman et al. |
| 2004/0049225 A1 | 3/2004 | Denison |
| 2004/0167553 A1 | 8/2004 | Simpson et al. |
| 2004/0167554 A1 | 8/2004 | Simpson et al. |
| 2004/0193034 A1 | 9/2004 | Wasicek et al. |
| 2004/0210245 A1 | 10/2004 | Erickson et al. |
| 2005/0004585 A1 | 1/2005 | Hall et al. |
| 2005/0004594 A1 | 1/2005 | Nool et al. |
| 2005/0021063 A1 | 1/2005 | Hall et al. |
| 2005/0042239 A1 | 2/2005 | Lipiecki et al. |
| 2005/0090845 A1 | 4/2005 | Boyd |
| 2005/0090849 A1 | 4/2005 | Adams |
| 2005/0177068 A1* | 8/2005 | Simpson ............... 600/564 |
| 2005/0216018 A1 | 9/2005 | Sennett |
| 2005/0222596 A1 | 10/2005 | Maschke |
| 2005/0222663 A1 | 10/2005 | Simpson et al. |
| 2006/0015126 A1 | 1/2006 | Sher |
| 2006/0235334 A1 | 10/2006 | Corvi et al. |
| 2006/0259052 A1 | 11/2006 | Pintor et al. |
| 2007/0010840 A1 | 1/2007 | Rosenthal et al. |
| 2007/0038061 A1 | 2/2007 | Huennekens et al. |
| 2007/0049958 A1 | 3/2007 | Adams |
| 2007/0135712 A1 | 6/2007 | Maschke |
| 2007/0135886 A1 | 6/2007 | Maschke |
| 2007/0167824 A1 | 7/2007 | Lee et al. |
| 2007/0225739 A1 | 9/2007 | Pintor et al. |
| 2007/0265647 A1 | 11/2007 | Bonnette et al. |
| 2007/0276419 A1 | 11/2007 | Rosenthal |
| 2008/0001643 A1 | 1/2008 | Lee |
| 2008/0004644 A1 | 1/2008 | To et al. |
| 2008/0004645 A1 | 1/2008 | To et al. |
| 2008/0004646 A1 | 1/2008 | To et al. |
| 2008/0004647 A1 | 1/2008 | To et al. |
| 2008/0045986 A1 | 2/2008 | To et al. |
| 2008/0051812 A1 | 2/2008 | Schmitz et al. |
| 2008/0065124 A1 | 3/2008 | Olson |
| 2008/0065125 A1 | 3/2008 | Olson |
| 2008/0097403 A1 | 4/2008 | Donaldson et al. |
| 2008/0125799 A1 | 5/2008 | Adams |
| 2008/0161840 A1 | 7/2008 | Osiroff et al. |
| 2008/0177139 A1 | 7/2008 | Courtney et al. |
| 2008/0208227 A1 | 8/2008 | Kadykowski et al. |
| 2008/0249553 A1 | 10/2008 | Gruber et al. |
| 2008/0312673 A1 | 12/2008 | Viswanathan et al. |
| 2009/0012548 A1 | 1/2009 | Thatcher et al. |
| 2009/0018565 A1 | 1/2009 | To et al. |
| 2009/0018566 A1 | 1/2009 | Escudero et al. |
| 2009/0138031 A1 | 5/2009 | Tsukernik et al. |
| 2009/0187203 A1 | 7/2009 | Corvi et al. |
| 2009/0216125 A1 | 8/2009 | Lenker |
| 2009/0216180 A1 | 8/2009 | Lee et al. |
| 2009/0226063 A1 | 9/2009 | Rangwala et al. |
| 2009/0234378 A1 | 9/2009 | Escudero et al. |
| 2009/0270888 A1 | 10/2009 | Patel et al. |
| 2009/0275966 A1 | 11/2009 | Mitusina |
| 2009/0299394 A1 | 12/2009 | Simpson et al. |
| 2009/0306689 A1 | 12/2009 | Welty et al. |
| 2010/0030216 A1 | 2/2010 | Arcenio |
| 2010/0049225 A1 | 2/2010 | To et al. |
| 2010/0130996 A1 | 5/2010 | Doud et al. |
| 2010/0198240 A1 | 8/2010 | Simpson et al. |
| 2010/0241147 A1 | 9/2010 | Maschke |
| 2010/0280534 A1 | 11/2010 | Sher |
| 2010/0292721 A1 | 11/2010 | Moberg |
| 2010/0298850 A1 | 11/2010 | Snow et al. |
| 2010/0312263 A1 | 12/2010 | Moberg et al. |
| 2011/0004107 A1 | 1/2011 | Rosenthal et al. |

(56) References Cited

U.S. PATENT DOCUMENTS

| | | |
|---|---|---|
| 2011/0022069 A1 | 1/2011 | Mitusina |
| 2011/0040315 A1 | 2/2011 | To et al. |
| 2011/0130777 A1 | 6/2011 | Zhang et al. |
| 2011/0144673 A1 | 6/2011 | Zhang et al. |

FOREIGN PATENT DOCUMENTS

| | | |
|---|---|---|
| DE | 8900059 U1 | 5/1989 |
| DE | 93 03 531 U1 | 7/1994 |
| DE | 44 44 166 A1 | 6/1996 |
| DE | 29722136 U1 | 5/1999 |
| EP | 0086048 A2 | 8/1983 |
| EP | 0 107 009 A2 | 5/1984 |
| EP | 0 229 620 A2 | 7/1987 |
| EP | 0291170 A1 | 11/1988 |
| EP | 0 302 701 A2 | 2/1989 |
| EP | 0330843 A1 | 9/1989 |
| EP | 0373927 A2 | 6/1990 |
| EP | 0421457 A1 | 4/1991 |
| EP | 0 431 752 A2 | 6/1991 |
| EP | 0448859 A2 | 10/1991 |
| EP | 0463798 A1 | 1/1992 |
| EP | 0 490 565 A1 | 6/1992 |
| EP | 0514810 A1 | 11/1992 |
| EP | 0 526 042 A1 | 2/1993 |
| EP | 0533320 A2 | 3/1993 |
| EP | 0 608 911 A1 | 8/1994 |
| EP | 0 608 912 A1 | 8/1994 |
| EP | 0 611 522 A1 | 8/1994 |
| EP | 0 648 414 B1 | 4/1995 |
| EP | 0657140 A1 | 6/1995 |
| EP | 0 680 695 B1 | 11/1998 |
| EP | 0 983 749 A2 | 3/2000 |
| EP | 1 767 159 A1 | 3/2007 |
| EP | 1 875 871 A2 | 1/2008 |
| GB | 2093353 A | 9/1982 |
| GB | 2 115 829 A | 9/1983 |
| GB | 2210965 A | 6/1989 |
| JP | 2-206452 A | 8/1990 |
| JP | 2271847 A | 11/1990 |
| JP | 3186256 A | 8/1991 |
| JP | 4200459 A | 7/1992 |
| JP | 5042162 A | 2/1993 |
| JP | 5056984 A | 3/1993 |
| JP | 5184679 A | 7/1993 |
| JP | 6269460 A | 9/1994 |
| JP | 7075611 B | 8/1995 |
| SU | 442795 A1 | 9/1974 |
| SU | 665908 A1 | 6/1979 |
| WO | WO 8906517 A1 | 7/1989 |
| WO | WO 92/07500 A2 | 5/1992 |
| WO | WO 9313716 A1 | 7/1993 |
| WO | WO 9313717 A1 | 7/1993 |
| WO | WO 93/16642 A1 | 9/1993 |
| WO | WO 9521576 A1 | 8/1995 |
| WO | WO 9611648 A1 | 4/1996 |
| WO | WO 9746164 A1 | 12/1997 |
| WO | WO 9804199 A1 | 2/1998 |
| WO | WO 9824372 A1 | 6/1998 |
| WO | WO 99/39648 A1 | 8/1999 |
| WO | WO 9952454 A1 | 10/1999 |
| WO | WO 00/30531 A1 | 6/2000 |
| WO | WO 00/54735 A1 | 9/2000 |
| WO | WO 00/62913 A1 | 10/2000 |
| WO | WO 00/63800 A1 | 11/2000 |
| WO | WO 00/72955 A1 | 12/2000 |
| WO | WO 01/15609 A1 | 3/2001 |
| WO | WO 01/19444 A1 | 3/2001 |
| WO | WO 0130433 A1 | 5/2001 |
| WO | WO 01/43857 A1 | 6/2001 |
| WO | WO 0143809 A1 | 6/2001 |
| WO | WO 02/16017 A2 | 2/2002 |
| WO | WO 02/45598 A2 | 6/2002 |
| WO | 02056776 A1 | 7/2002 |
| WO | 03090630 A2 | 11/2003 |
| WO | WO 2006/058223 A2 | 6/2006 |
| WO | WO 2006/066012 A2 | 6/2006 |

OTHER PUBLICATIONS

Jan. 18, 2012 PCT International Search Report and Written Opinion in Application No. PCT/US2011/058107 (19 pages).

Abstract of JP2206452A (1 page).

Amplatz Coronary Catheters, posted: Feb. 25, 2009, [online], [retrieved on Mar. 29, 2011], retrieved from the Cardiophile MD using Internet website <URL:http://cardiophile.org/2009/02/amplatzcoronary-catheter.html> (3 pages).

Judkins Left Coronary Catheter, posted: Feb. 19, 2009, [online], [retrieved on Mar. 29, 2011], retrieved from the Cardiophile MD using Internet website <URL:http://cardiophile.org/2009/02/judkins-left-coronary-catheter.html> (3 pages).

Translation of Aug. 15, 2007 mailed Japanese Patent Office Action, Application No. 1999-139033 (4 pages).

Abstract of DE 44 44 166 A1 (1 page).

Brezinski et al., "Optical Coherence Tomography for Optical Biopsy," Circulation, 93:1206-1213 (1996).

Brezinski et al., "Assessing Atherosclerotic Plaque Morphology: Comparison of Optical Coherence Tomography and High Frequency Intravascular Ultrasound," Heart, 77:397-403 (1997).

Huang et al., "Optical Coherence Tomography," Science, 254:1178-1181 (1991).

International Search Report and Written Opinion of PCT Application No. PCT/US04/12600, dated Jun. 13, 2008, 8 pages total.

International Search Report of PCT Application No. PCT/US04/12601, dated Jun. 30, 2005, 3 pages total.

Mar. 27, 2009 Communication from the European Patent Office regarding EP Application No. 01 991 343.3 (7 pages).

Apr. 6, 2010 European Supplementary Search Report in European Application No. 04760156.2 (3 pages).

Sep. 21, 2010 International Search Report and Written Opinion for corresponding PCT Application No. PCT/US2010/032558 (14 pages).

Exam Report issued May 16, 2013 in related Canadian Patent Application No. 2,760,449, 3 pgs.

Notice of Reasons for Rejection issued Nov. 18, 2013 in related Japanese Patent Application No. 2012-508588, 7 pages, with English translation.

Notification of the First Office action for Chinese Application No. 201080026742.1 dated Jan. 30, 2014, including Search Report, 20 pages, English translation included.

Exam Report in related Canadian Patent Application No. 2,760,449, Apr. 3, 2014, 2 pages, Canada.

Exam Report in related Canadian Patent Application No. 2,760,449, Jan. 23, 2015, 3 pages, Canada.

\* cited by examiner

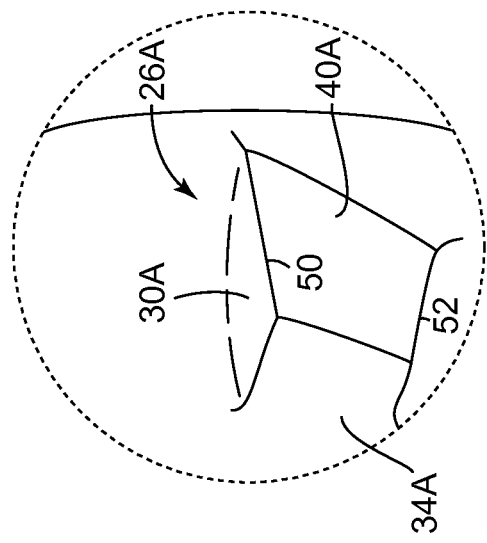
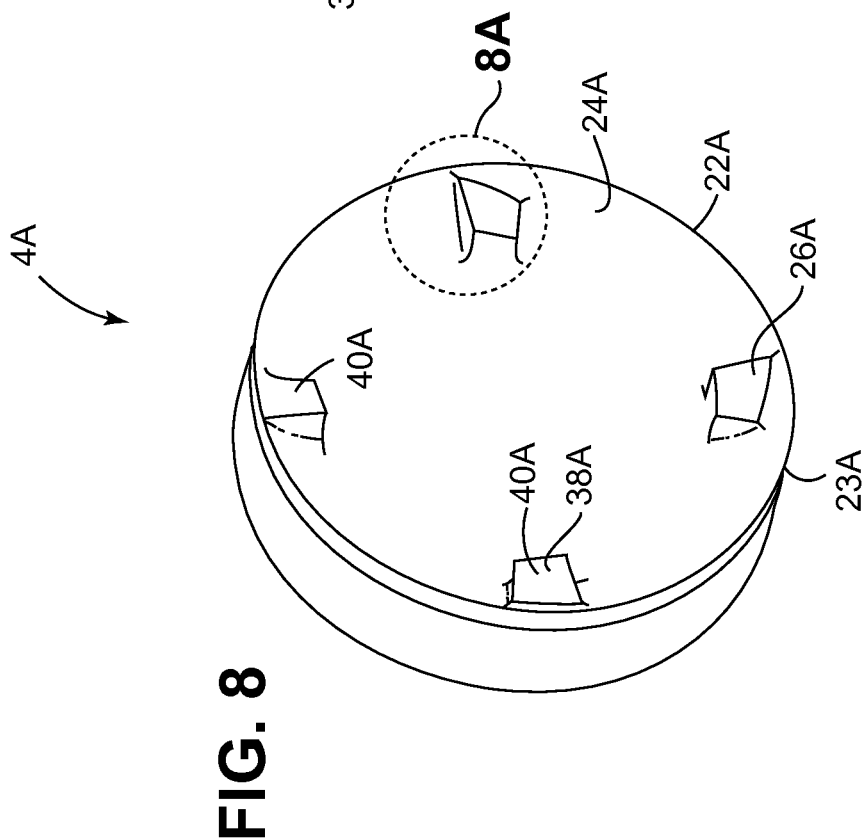
FIG. 8A
FIG. 8

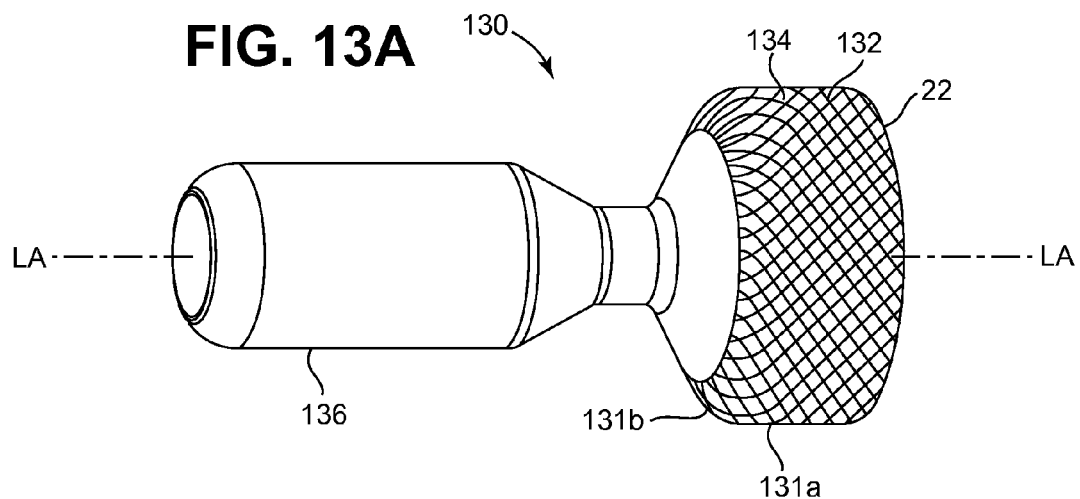
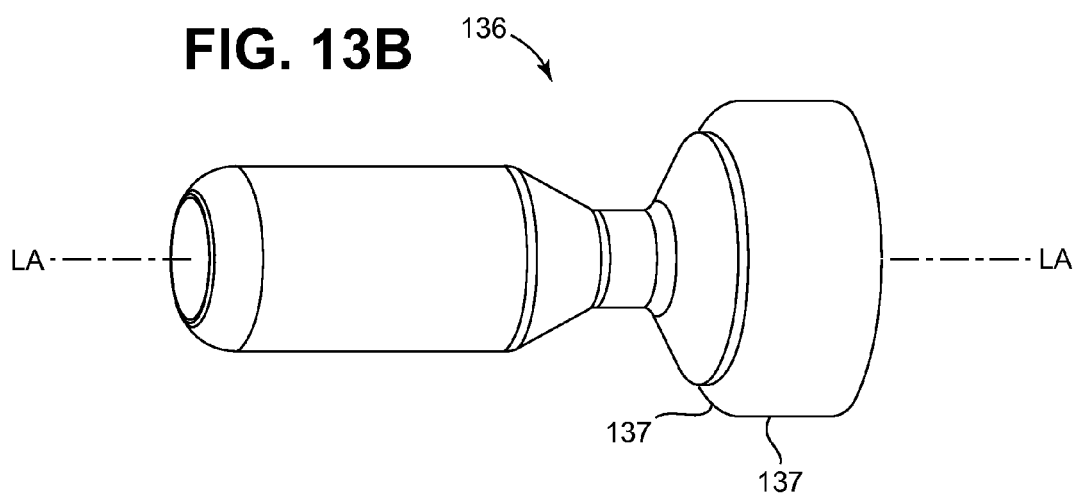

METHODS AND DEVICES FOR CUTTING AND ABRADING TISSUE

This application claims the benefit of U.S. Provisional Patent Application No. 61/173,845, filed Apr. 29, 2009, entitled "Methods and Devices for Cutting/Abrading Tissue", the contents of which are hereby incorporated by reference herein.

FIELD OF THE INVENTION

The present invention relates to catheters used to remove material from a site in a body lumen. More particularly, this invention pertains to cutters capable of removing both soft and hard material from the site.

BACKGROUND OF THE INVENTION

Atherosclerosis is a progressive disease of the vascular system whereby atheroma is deposited on the inner walls of blood vessels. Over time atheromatous deposits can become large enough to reduce or occlude blood flow through the vessels, leading to symptoms of low blood flow such as pain in the legs (on walking or at rest), skin ulcer, angina (at rest or exertional), and other symptoms. To treat this disease and improve or resolve these symptoms it is desirable to restore or improve blood flow through the vessel.

Various means are used to restore or improve blood flow through atheromatous vessels. The atheroma deposits can be displaced by diametrically expanding the vessel by inflating balloons, expanding stents, and other methods. However these methods undesirably tear and stretch the vessel, causing scar formation in a high percentage of patients. Such scar tissue (restenotic material), once formed, blocks flow in the vessel and often needs to be removed. The deposits can be pulverized using lasers and other methods. However pulverization alone of atheromatous material allows microemboli to flow downstream and lodge in distal vascular beds, further compromising blood flow to the tissue affected by the disease. Atherectomy catheters can be used to remove atheromatous deposits from the blood vessel and can present an ideal solution when the atheromatous debris removed from the vessel is captured and removed from the body.

One problem that occurs when removing material from a blood vessel is that the material may be either soft or hard. Typically, restenotic scar is soft yet tough while atheroma varies in texture from soft with little structure, to soft yet fibrotic, to densely fibrotic (hard). Any or all of these restenotic or atheromatous tissues may be calcified and the calcified tissues can be extremely hard. The hardness and toughness characteristics of the material needing to be cut from the vessel may vary along the length of the vessel, around the circumference of the vessel, or both. Further, the portion of the vessel to be treated can be quite extensive. For example, the portion of the vessel to be treated can extend over a vessel length of 200 mm or longer. As such, the cutting element of an atherectomy catheter should be able to cut both hard tissue and soft tissue.

SUMMARY OF THE INVENTION

The invention provides an atherectomy catheter comprising: a body having an opening; a rotatable shaft coupled to the body; a tissue collection chamber coupled to the body and positioned distal to the cutting element; and a cutting element coupled to the rotatable shaft for rotating the shaft about a longitudinal axis, the cutting element having a cup-shaped surface and a cutting edge, the cup-shaped surface being configured to re-direct tissue cut by the cutting edge in a distal direction when the cup-shaped surface moves in the distal direction, and the cutting element having at least one abrasive surface. The invention also provides a method of removing material from a body lumen, the method comprising: providing an atherectomy catheter, placing the catheter in the body lumen; and moving the catheter in the body lumen to contact the cutting element with the material in the body lumen.

The present invention provides an atherectomy catheter which has a cutting element that is able to cut both soft tissue and hard tissue, and methods of cutting material from a blood vessel lumen using a rotating cutting element. The cutting element has a sharp cutting edge that surrounds a cup-shaped surface and at least one surface of abrasive material. The cup-shaped surface directs the cut material into a tissue chamber. The circumferential cutting edge and the cup-shaped surface together are well suited to cut and remove relatively soft tissue from the blood vessel. The abrasive material surface in combination with the cutting element is well suited to abrade and remove hard material from the blood vessel.

These and other aspects of the invention will become apparent from the following description of the preferred embodiments, drawings and claims. The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIGS. 8 and 8A illustrate an isometric view of the raised elements of the cutting element of FIG. 7.

FIGS. 13A, 13B, 14A, 14B, 15A and 15B illustrate isometric views of other embodiments of cutters and cutter subassemblies suitable for use with the atherectomy catheter illustrated in FIG. 1.

DETAILED DESCRIPTION

Figure 1:
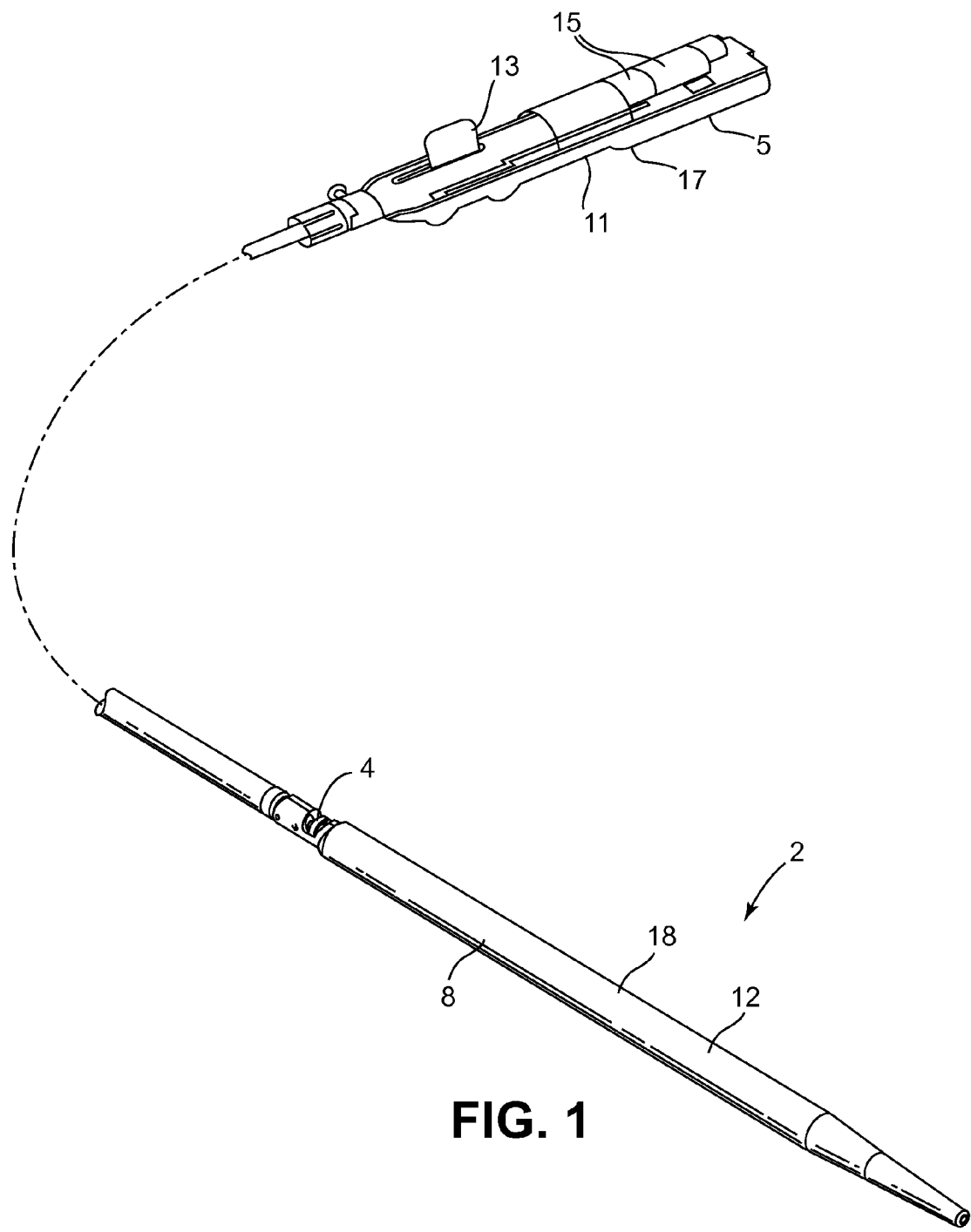
FIG. 1 illustrates an isometric view of an atherectomy catheter.
Figure 2:
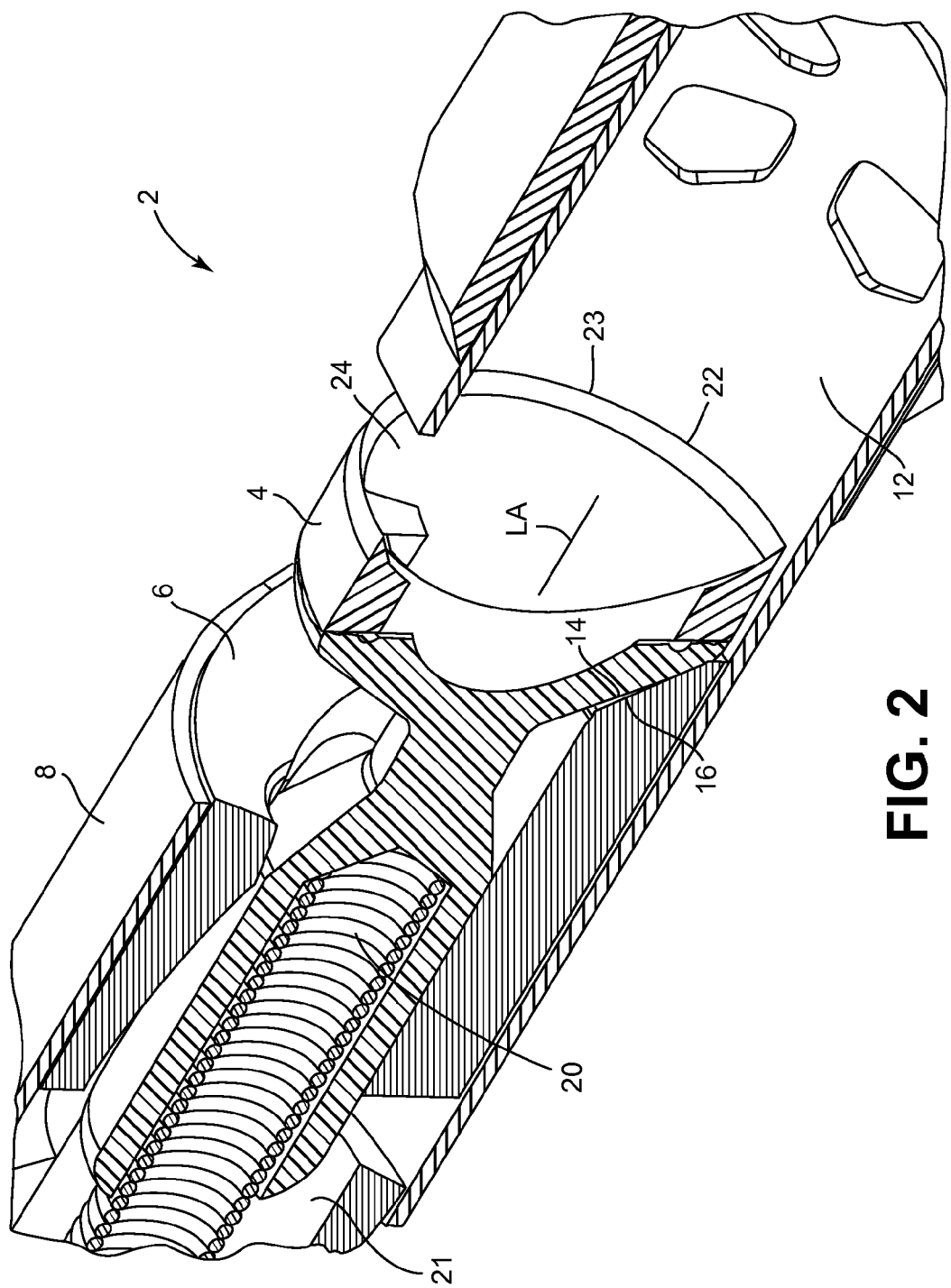
FIG. 2 illustrates an isometric cross-sectional view of a portion of the atherectomy catheter illustrated in FIG. 1 with a cutting element in a stored position.
Figure 3:
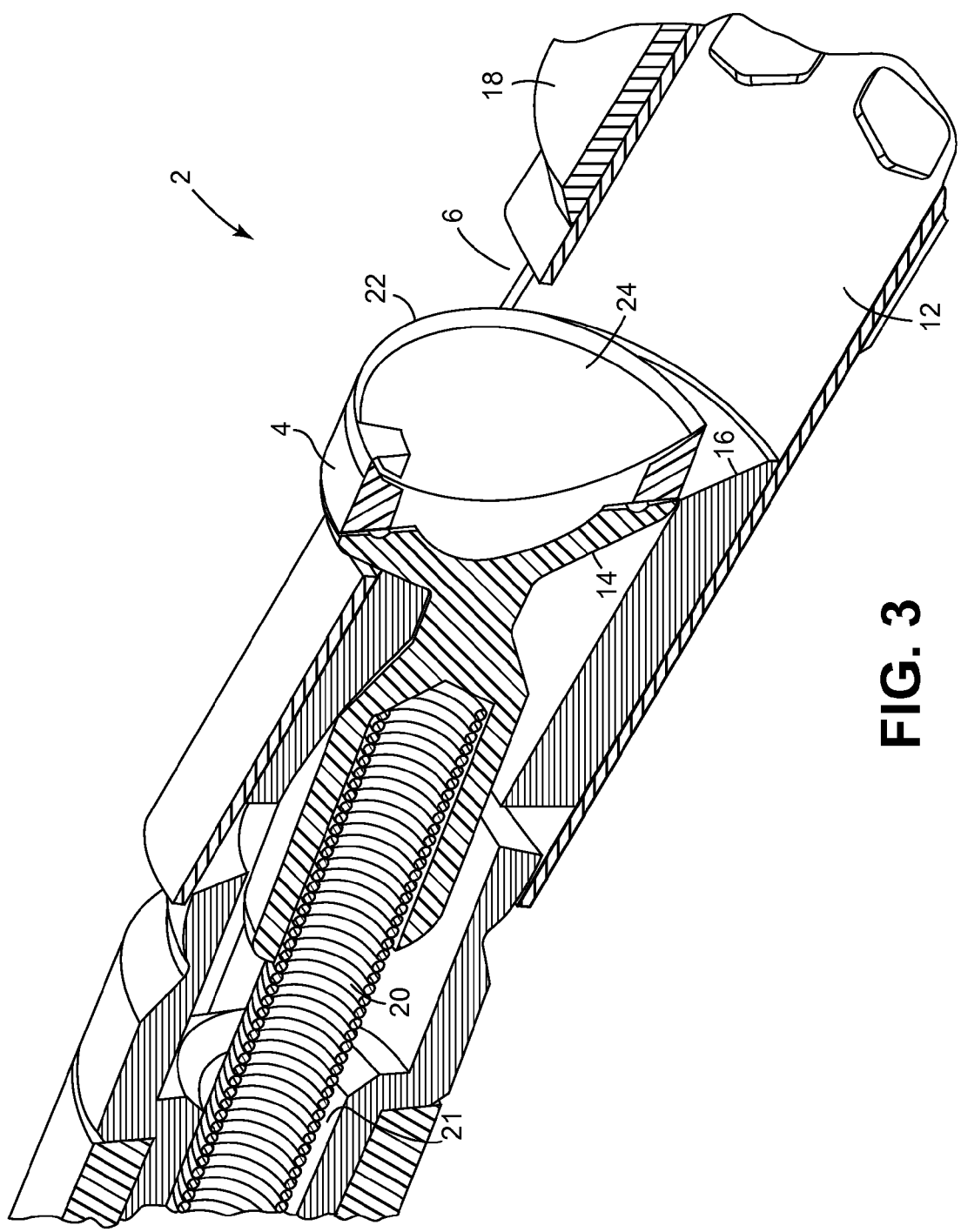
FIG. 3 illustrates an isometric cross-sectional view of a portion of the atherectomy catheter illustrated in FIG. 1 with a cutting element in a working position.

The invention provides an atherectomy catheter comprising: a body having an opening; a rotatable shaft coupled to the body; a tissue collection chamber coupled to the body and positioned distal to the cutting element; and a cutting element coupled to the rotatable shaft for rotating the shaft about a longitudinal axis, the cutting element having a cup-shaped surface and a cutting edge, the cup-shaped surface being configured to re-direct tissue cut by the cutting edge in a distal direction when the cup-shaped surface moves in the distal direction, and the cutting element having at least one abrasive surface. In one embodiment, the cutting edge is a radially outer edge of the cutting element. In an embodiment, the catheter comprises a raised element extending outwardly from the cup-shaped surface of the cutting element. In one embodiment, the cutting edge is a radially outer edge of the cutting element and the raised element is recessed proximally from the cutting edge when viewed along the longitudinal axis.

In an embodiment, the cutting element is movable between a stored position and a cutting position relative to the opening. In one embodiment, the cutting element is moved between the stored position and the cutting position by sliding the cutting element against a cam surface. In an embodiment, a distal portion of the catheter relative to a proximal portion is deflected by sliding the cutting element against the cam surface.

In embodiments of the invention, the abrasive surface is flush, recessed, or elevated in relation to adjacent non-abrasive cutting element surfaces. In an embodiment of the invention, the cutting element has a major diameter D in the range of 0.030 to 0.100" (0.076 to 0.25 cm). In one embodiment, the cutting element has a major diameter D of 0.061" (0.15 cm). In an embodiment, the cutting element comprises one abrasive surface, and in another embodiment the cutting element comprises two or more abrasive surfaces. The two or more abrasive surfaces can comprise at least two surfaces having different abrasive properties. In one embodiment, the abrasive surface is comprised of abrasive material that has been attached to the cutting element. The abrasive material may comprise diamond plate. In one embodiment, the abrasive material has a particle size of 10 to 800 microns. In one embodiment, the abrasive surface has been produced without attaching abrasive materials to the cutting element. The abrasive surface can be produced by knurling, grit blasting, etching, or laser ablation.

In an embodiment of the invention, the abrasive surface is on at least a portion of an outer, major diameter surface of the cutting element. The outer, major diameter surface may be parallel to a longitudinal axis LA of the cutting element. In one embodiment, the abrasive surface is on a proximal shoulder surface of the cutting element. In an embodiment, one or more abrasive surfaces are on the entire outer, major diameter surface of the cutting element. In an embodiment of the invention, the abrasive surface is on at least the cup-shaped surface. In another embodiment, the abrasive surface is on the raised element. In another embodiment, the cutting element comprises two or more abrasive surfaces having different abrasive properties and the at least two surfaces having different abrasive properties are both on a portion of an outer, major diameter surface of the cutting element.

The invention also provides a method of removing material from a body lumen, the method comprising: providing an atherectomy catheter, placing the catheter in the body lumen; and moving the catheter in the body lumen to contact the cutting element with the material in the body lumen. In one embodiment, the catheter is moved in a distal direction to contact the cutting edge with the material in the body lumen. In another embodiment, the catheter is moved in a proximal direction to contact the abrasive surface with the material in the body lumen. In an embodiment, the abrasive surface is on a proximal shoulder surface of the cutting element. In an embodiment, the catheter is placed in the body lumen with the cutting element in the stored position and the catheter is moved to contact the material with the cutting element in a cutting position.

Referring to FIGS. 1 to 4, an atherectomy catheter 2 is shown which has a cutting element 4, which is used to cut material from a blood flow lumen such as a blood vessel. The cutting element 4 is movable between a stored position (FIG. 2) and a cutting position (FIG. 3) relative to an opening 6 in a body 8 of the catheter 2. The cutting element 4 moves outwardly relative to the opening 6 so that a portion of the element 4 extends outwardly from the body 8 through the opening 6. In one embodiment the cutting element 4 may be positioned relative to the body 8 and opening 6 so that less than 90 degrees of the cutting element 4 is exposed to cut tissue. In other embodiments more of the cutting element 4 may be exposed without departing from numerous aspects of the invention.

Distal end of catheter 2 is positioned near a treatment site of a vessel with cutting element 4 in the stored position. Then catheter 2 is moved distally through the vessel with the cutting element 4 in the working or cutting position as described in further detail below. As the catheter 2 moves through the blood vessel with the cutting element 4 in the working or cutting position the tissue material is cut by the cutting element 4 and is directed into a tissue chamber 12 positioned distal to the cutting element 4. The tissue chamber 12 may be somewhat elongated to accommodate the tissue which has been cut.

To expose cutting element 4 through opening 6 cutting element 4 is moved proximally from the stored position so that a cam surface 14 on the cutting element 4 engages a ramp 16 on the body 8 of the catheter 2. The interaction between the cam surface 14 and the ramp 16 causes the cutting element 4 to move to the cutting position and also causes a tip 18 to deflect which tends to move the cutting element 4 toward the tissue to be cut.

The cutting element 4 is coupled to a shaft 20 that extends through a lumen 21 in the catheter 2. Catheter 2 is coupled to exemplary cutter driver 5. Cutter driver 5 is comprised of motor 11, power source 15 (for example one or more batteries), microswitch (not shown), housing 17 (upper half of housing is removed as shown), lever 13 and connection assembly (not shown) for connecting shaft 20 to driver motor 11. Cutter driver 5 can act as a handle for the user to manipulate catheter 2. Lever 13, when actuated to close a microswitch, electrically connects power source 15 to motor 11 thereby causing rotation of cutting element 4. The cutting element 4 is rotated about a longitudinal axis LA when the shaft 20 rotates. The cutting element 4 is rotated about 1 to 160,000 rpm but may be rotated at any other suitable speed depending upon the particular application. Further description of catheters similar to catheter 2 are found in U.S. patent application Ser. No. 10/027,418 (published as US 2002/0077642 A1) to Patel et al., entitled "Debulking Catheter", the contents of which are incorporated by reference herein.

Figure 5:
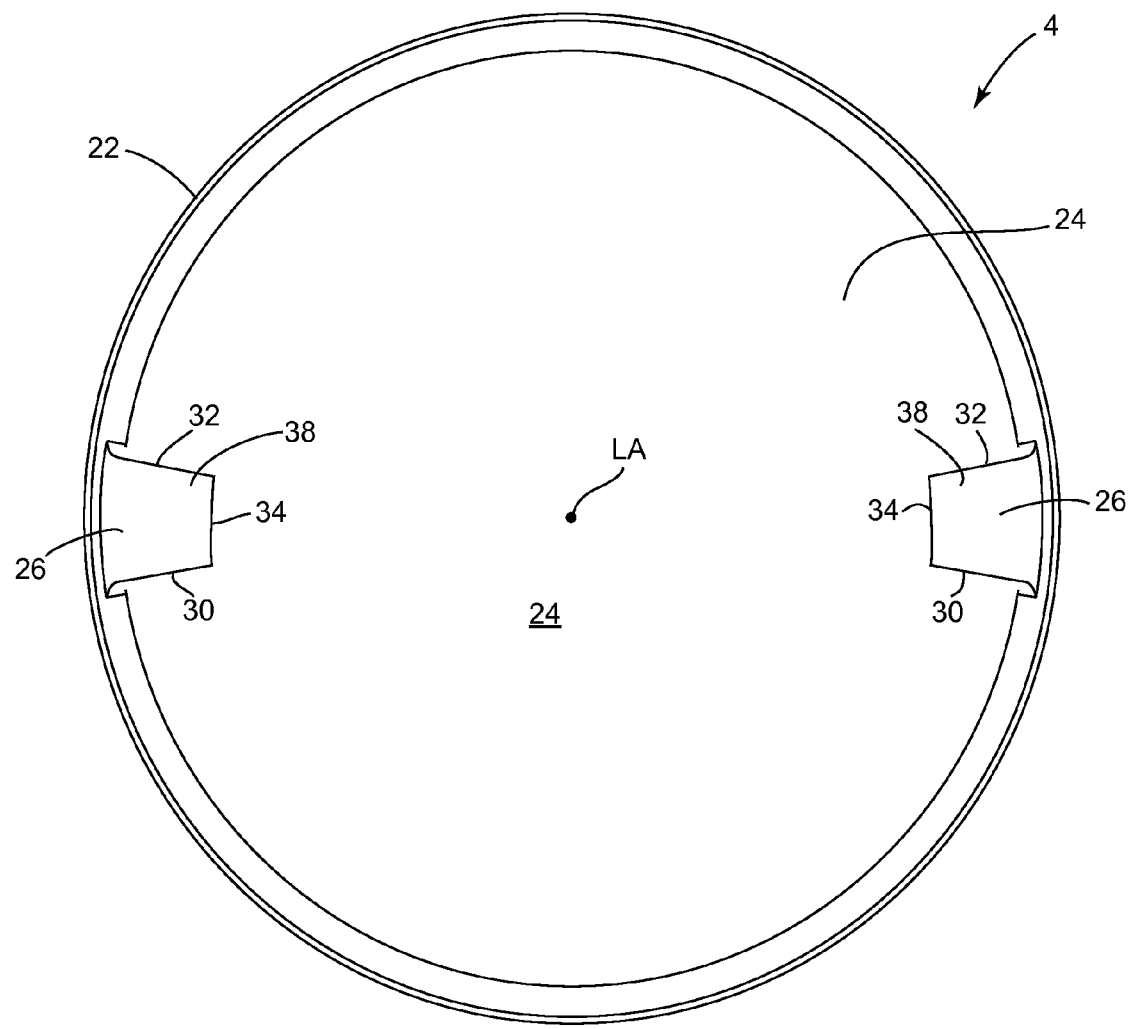
FIG. 5 illustrates an end view of an embodiment of a cutting element.

Referring to FIG. 5, the cutting element 4 is shown when viewed along the longitudinal axis LA. The term "along the longitudinal axis" as used herein shall mean for example the view of FIG. 5 that shows the distal end of the cutting element 4 when viewed in the direction of the longitudinal axis and/or the axis of rotation. The cutting element 4 has a cutting edge 22 that may be a continuous, uninterrupted, circular-shaped edge although it may also include ridges, teeth, serrations or other features without departing from the scope of the invention. The cutting edge 22 may be at a radially outer edge 23 of the cutting element 4 when the cutting element 4 is in the cutting position.

The cutting element 4 has a cup-shaped surface 24, which directs the tissue cut by the cutting edge 22 into the tissue chamber 12. The cup-shaped surface 24 may be a smooth and continuous surface free of throughholes, teeth, fins or other features, which disrupt the smooth nature of the surface 24 for at least half the distance from the longitudinal axis LA to the outer radius at the cutting edge 22. The cup-shaped surface 24 may also be free of any such features throughout an area of at least 300 degrees relative to the longitudinal axis LA.

Figure 4:
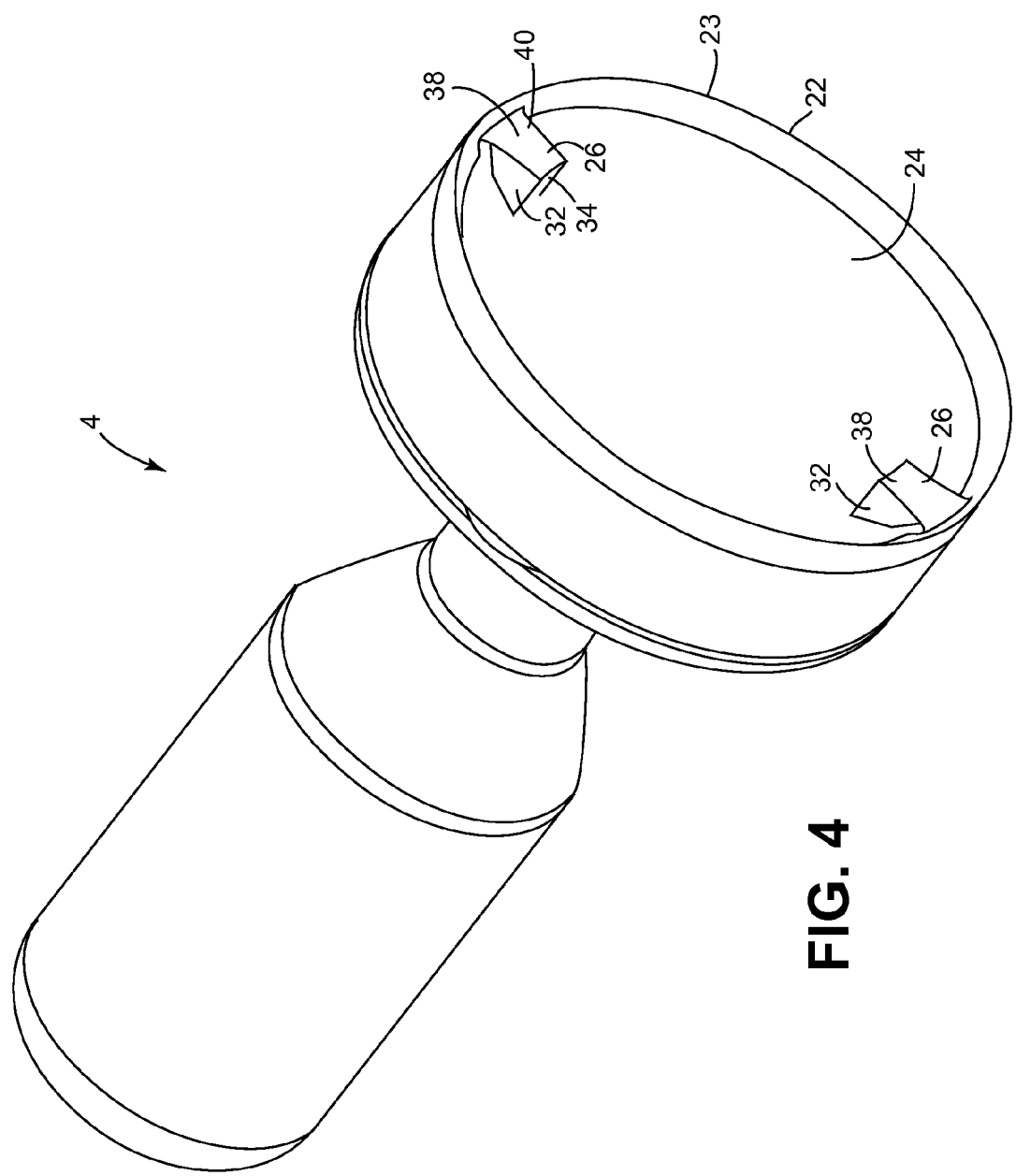
FIG. 4 illustrates an isometric view of an embodiment of a cutting element.
Figure 6:
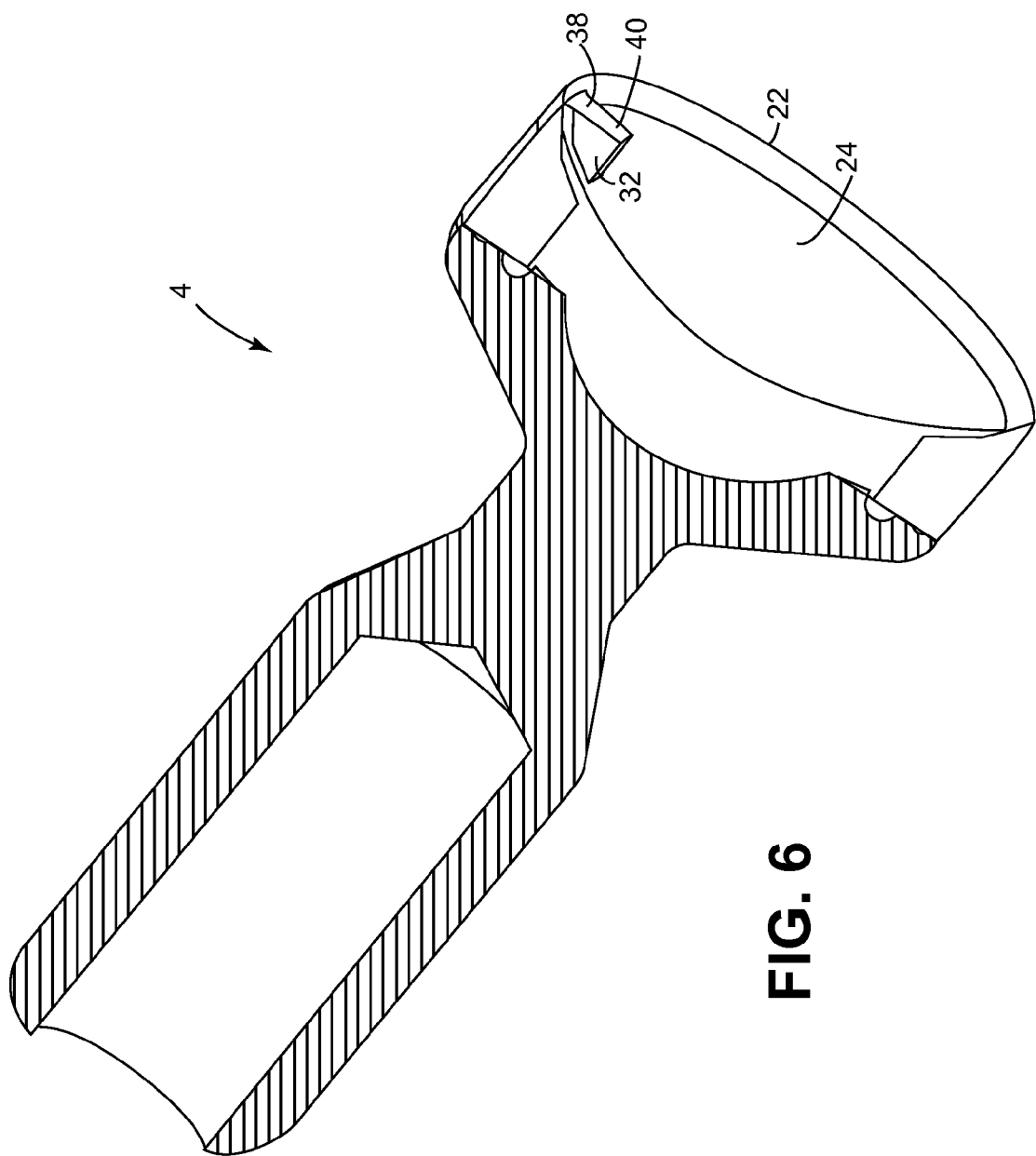
FIG. 6 illustrates an isometric cross-sectional view of an embodiment of a cutting element.

Referring to FIGS. 4 to 6, one or more raised elements 26 extend outwardly from the cup-shaped surface 24 with FIG. 5 showing two raised elements 26. The raised element 26 is a small wedge of material that rises relatively abruptly from the cup-shaped surface 24. The raised element 26 has a first wall 30 and a second wall 32 that both extend radially and form an angle of about 20 degrees therebetween so that the two raised elements 26 together occupy an area of about 40 degrees and altogether may be less than 60 degrees. A third wall 34 extends between the radially inner portion of the first and second walls 30, 32. The raised element 26 helps to break up hard tissue and plaque by applying a relatively blunt force to the hard tissue or plaque since cutting such tissue with the cutting edge 22 is often not effective.

The raised elements 26 altogether occupy a relative small part of the cup-shaped surface 24. The raised elements 26 together may occupy less than 5% of a surface area of the cutting element 4. The term "surface area of the cutting element" as used herein shall mean the surface area which is radially inward from the outer or cutting edge 22 and is exposed when viewed along the longitudinal axis LA. Stated another way, at least 95% of the surface area of the cutting element is a smooth cup-shaped surface when viewed along the longitudinal axis. By sizing and positioning the raised element 26 in this manner, the raised element 26 does not interfere with the ability of the cutting element 4 to cut and re-direct tissue into the tissue chamber while still providing the ability to break up hard tissue and plaque with the raised element 26.

The raised element 26 may be recessed from the cutting edge 22 longitudinally and/or radially. The raised element 26 may be recessed longitudinally from the cutting edge 0.0010 to 0.0020 inch (0.0025 to 0.0051 cm) and may be about 0.0015 inch (0.0038 cm). The raised element 26 may be recessed radially from the cutting edge 22 by about the same amount. A distal wall 38 of the cutting element 4 forms a flat surface 40, which is perpendicular to the longitudinal axis LA so that the entire surface is recessed the same distance from the cutting edge. The distal wall 38 may take any other shape, such as a curved shape, or may be tilted, inclined or beveled as now described.

Figure 7:
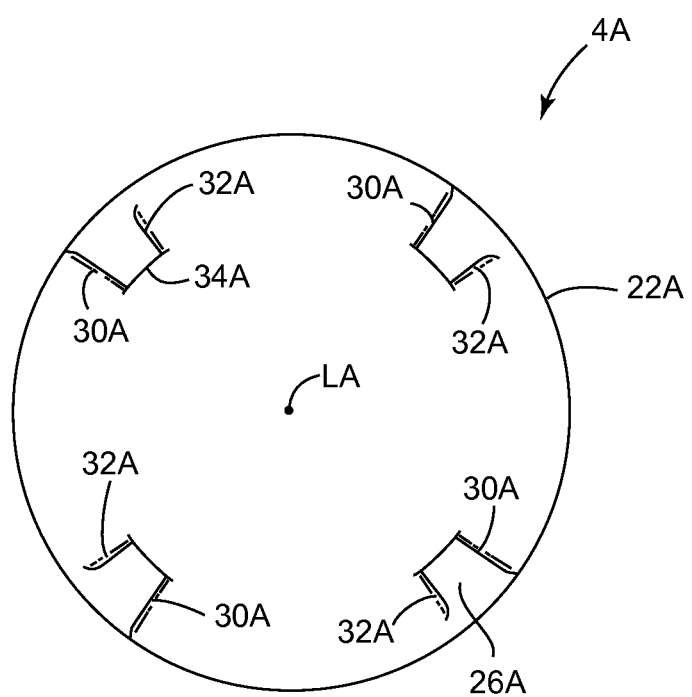
FIG. 7 illustrates an end view of another embodiment of a cutting element, which may be used with the atherectomy catheter of FIG. 1.

Referring to FIGS. 7 and 8, another cutting element 4A is shown wherein the same or similar reference numbers refer to the same or similar structure and all discussion concerning the same or similar features of the cutting element 4 are equally applicable here. The cutting element 4A has a cutting edge 22A that may be a continuous, uninterrupted, circular-shaped edge although it may also include ridges, teeth, serrations or other features without departing from the scope of the invention. The cutting edge 22A may be at a radially outer edge 23A of the cutting element 4A when the cutting element 4A is in the cutting position. The cutting element 4A has a cup-shaped surface 24A that directs the tissue cut by the cutting edge 22A into the tissue chamber 12 (see FIG. 2). The cup-shaped surface 24A may be a substantially smooth and continuous surface as described above in connection with the cutting element 4.

One or more raised elements 26A extend outwardly from the cup-shaped surface 24A. FIG. 8 shows four raised elements 26A but may include any number such as 2, 3, 4, 6 or 8 raised elements. The raised element 26A is a small wedge of material that rises relatively abruptly from the cup-shaped surface 24A. The raised element 26A has a first wall 30A and a second wall 32A which both extend radially and form an angle of about 1 to 30 degrees therebetween so that the four raised elements 26A together occupy an area of about 4 to 60 degrees and altogether may be less than 60 degrees altogether. A third wall 34A extends between the radially inner portion of the first and second walls 30A, 32A. The raised elements 26A may occupy a relative small part of the cup-shaped surface 24A and may be recessed from the cutting edge 22A in the manner described above in connection with the cutting element 4.

A distal wall 38A of the cutting element 4A has a surface 40A that forms an angle of about 30 to 90 degrees with respect to the longitudinal axis LA. The entire surface 40A may still be somewhat close to but recessed from the cutting edge 22A so that the entire surface 40A is 0.0010 to 0.0050 inch (0.0025 to 0.013 cm) from the cutting edge. An edge 50 formed at the intersection of wall 30A and distal wall 38A is closer to the cutting edge 22A than an edge 52 formed at the intersection of wall 32A and distal wall 38A. The cutting element 4A may be rotated in either direction so that the raised edge 50 may be the leading or trailing edge. The raised edge may be 0.0010 to 0.0020 inch from the cutting edge. The raised elements 26A may all be formed in the same manner or may be different from one another. For example, some of the elements 26A could be angled in different directions so that two of the elements have the raised edge 50 as the leading edge and two of the elements 26A have the raised edge 50 as the trailing edge. The raised elements 26A may also subtend different angles, be of different heights or may have different radial lengths without departing from various aspects of the present invention.

Use of the catheter 2 is now described in connection with the cutting element 4 but is equally applicable to use of the catheter 2 with the cutting element 4A. The catheter 2 is introduced into the patient in a conventional manner using a guidewire (not shown) or the like. The catheter 2 is advanced over the guidewire with the cutting element in the stored position of FIG. 2 until the catheter is positioned at the location where material is to be removed. The cutting element 4 is then moved proximally so that the ramp 16 and cam surface 14 engage to move the cutting element 4 to the cutting position of FIG. 3 and to deflect the tip of the catheter 2 to move the cutting element 4 toward the tissue to be cut. The cutting element 4 is rotated about longitudinal axis LA and catheter 2 is then moved distally through the vessel so that the cutting element 4 cuts tissue. The tissue, which has been cut, is directed into the tissue chamber 12.

Figure 9:
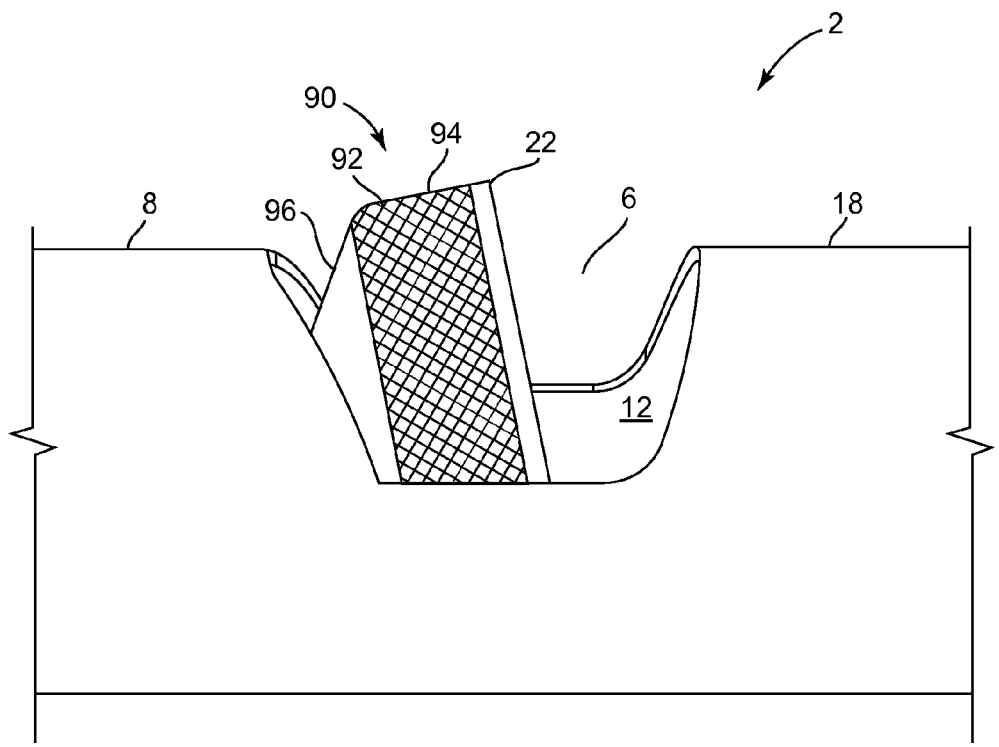
FIG. 9 illustrates an isometric side view of a portion of the atherectomy catheter illustrated in FIG. 1 with another embodiment of a cutting element in a working position.

FIGS. 9 to 17 illustrate further embodiments of cutting elements well suited to cut and remove from a blood vessel both relatively soft tissue and relatively hard tissue. Any of cutting elements 90, 100, 130, 140, 150a, 150b, 160 may be substituted in place of cutting element 4, 4A of catheter 2. In one example FIG. 9 illustrates cutting element 90 assembled into catheter 2, with cutting element 90 exposed through window 6 in a working or cutting position. In FIGS. 9, 10, 11, 13A, 14A, 15A, 15B, 16A and 17 abrasive surfaces 92, 102, 102', 132, 142, 152a, 152b, 162a, 162b are schematically illustrated by means of not-to-scale cross hatching. In various embodiments abrasive surfaces are flush with, elevated in relation to, or recessed in relation to adjacent non-abrasive cutting element surfaces.

Cutting elements 90, 100, 130, 140, 150a, 150b, 160 are comprised of cutting blade 22, abrasive surface 92, 102, 102', 132, 142, 152a, 152b, 162a, 162b, cutter blank 96, 106, 106', 136, 146, 156a, 156b, 166, and may be comprised of abrasive materials 94, 104, 104', 134, 144, 154a, 154b, 164a, 164b. Cutting element major diameter D (see, for example, FIG. 10) is contemplated to be in the range of 0.030" to 0.100" (0.076 to 0.25 cm). In one embodiment, cutting element major diameter is 0.061" (0.15 cm). In other embodiments cutting element major diameter is 0.035", 0.040", 0.043", 0.050", 0.055", 0.065", 0.069", 0.075", 0.080" or 0.090" (0.089 cm, 0.10 cm, 0.11 cm, 0.13 cm, 0.14 cm, 0.17 cm, 0.18 cm, 0.19 cm, 0.20 cm, or 0.23 cm). While cutting element 90, 100, 130, 140, 150a, 150b, 160 major diameter D (for example, see FIG. 10) is generally illustrated as comprised of a cylinder having parallel sides, it is contemplated that the abrasive surface in the vicinity of the major diameter may be concave towards axis LA-LA, convex towards axis LA-LA, or may have other shapes.

Cutting blade 22 may be comprised of hard, tough, abrasion resistant materials such as steel, tungsten carbide, tungsten carbide loaded with 5% to 20% nickel, silicon carbide, titanium nitride, or other materials and may be produced by processes comprised of heat treating, ion implantation, grinding, honing, sharpening, Electrostatic Discharge Machining (EDM) and other processes. In one embodiment cutting blade 22 is comprised of tungsten carbide loaded with 15% nickel. Cutter blank 96, 106, 106', 136, 146, 156a, 156b, 166 may be comprised of hardened steel, stainless steel, titanium and its alloys, or other materials and may be comprised of one or more recessed or reduced diameter (as compared to cutting element major diameter D—see for example FIG. 10) regions 107, 137, 147, 167a, 167b into which abrasive materials may be secured. In one embodiment the cutter blank is comprised of full hardened #465 stainless steel.

Abrasive materials 94, 104, 104', 134, 144, 154a, 154b, 164a, 164b may be comprised of hard, particulate materials such as diamond, silicon carbide, aluminum oxide, tungsten carbide, metal, hardened steel or other materials, having a range of particle sizes and may be defined by grit size. In one embodiment the abrasive materials have a particle size of 40 microns. In other embodiments abrasive materials having particle sizes of 10, 20, 75, 100, 200, 300, 400, 500, 600, 700 or 800 microns are contemplated. In some embodiments the abrasive materials have grit sizes ranging from P2000 to P24 or anywhere in between as defined by ISO Standard 6344. In further embodiments the abrasive materials have grit sizes ranging from 1000 to 24 or anywhere in between as defined by the Coated Abrasive Manufacturers Institute (CAMI). In some embodiments abrasive materials may be attached to cutter blank 96, 106, 106', 136, 146, 156a, 156b, 166 by means of adhesive bonding, soldering, brazing, welding, sintering, diffusion bonding, plating, press fit or other means. In some embodiments abrasive surface 92, 102, 102', 132, 142, 152a, 152b, 162a, 162b is formed into cutter blank 96, 106, 106', 136, 146, 156a, 156b, 166 without the use of abrasive materials by processes such as knurling, grit blasting, etching, laser ablation and other processes. In one embodiment abrasive material 94, 104, 104', 134, 144, 154a, 154b, 164a, 164b is comprised of diamond plate.

Figure 17:
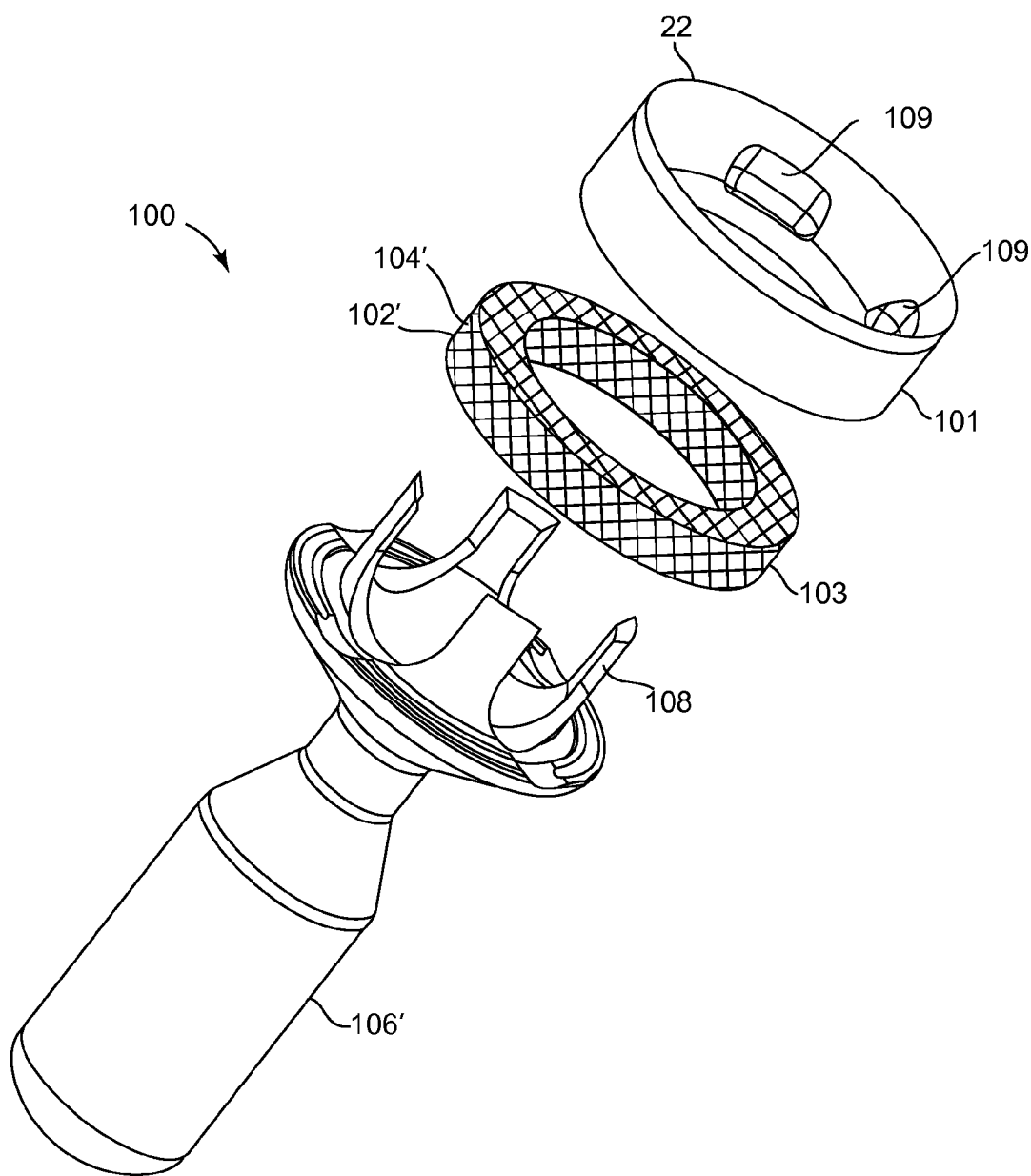
FIG. 17 illustrates an isometric view of another embodiment of a subassembly used to produce the cutting element illustrated in FIG. 11.

In another embodiment FIG. 17 illustrates an exemplary method for producing cutting elements 90, 100, 130, 140, 150a, 150b, 160. While the method is illustrated in the figure using cutting element 100 as an example, it is contemplated that the method with minor modification can be used to produce other cutting elements herein described. In the method, cutting element 100 is comprised of cutter preform 101, abrasive material preform 103 and cutter blank 106'. Cutter preform 101, abrasive material preform 103 and cutter blank 106' are comprised of the same materials and processes described above for cutting blade 22, abrasive materials 94, 104, 104', 134, 144, 154a, 154b, 164a, 164b and cutter blank 96, 106, 106', 136, 146, 156a, 156b, 166 respectively. Cutter preform 101 is further comprised of through holes 109 and cutter blank 106' is further comprised of fingers 108 which are slidably received within through holes 109. Fingers 108 are configured to slide within inner diameter of preform 103.

To assemble cutting element 100 using the method illustrated in FIG. 17 cutter preform 101, abrasive material preform 103 and cutter blank 106' are prefabricated as individual components. Thereafter abrasive material preform 103 is slid over fingers 108 and cutter preform 101 is slid over fingers 108 with fingers 108 slidably received in through holes 109, thereby sandwiching abrasive material preform 103 between cutter preform 101 and cutter blank 106'. Fingers are next secured to cutter preform 101 by means of processes or a combination of processes such as adhesive bonding, soldering, brazing, welding, sintering, diffusion bonding, mechanically deforming the fingers, or other processes. Advantages of the assembly method described are that the cutter preform 101, abrasive material preform 103 and cutter blank 106' can be comprised of different materials, and can be processed by different methods. Also by using the method, cutting elements such as cutting element 100 can be assembled from relatively inexpensive components.

One or more surfaces of cutting element 90, 100, 130, 140, 150a, 150b, 160 may be comprised of an abrasive surface 92, 102, 102', 132, 142, 152a, 152b, 162a, 162b including but not limited to, if present, the outer diameter, major diameter, minor diameter, concave surface, convex surface, raised elements, and other surfaces. Exemplary cutters having various configurations of abrasive surfaces are illustrated and discussed below.

Figure 10:
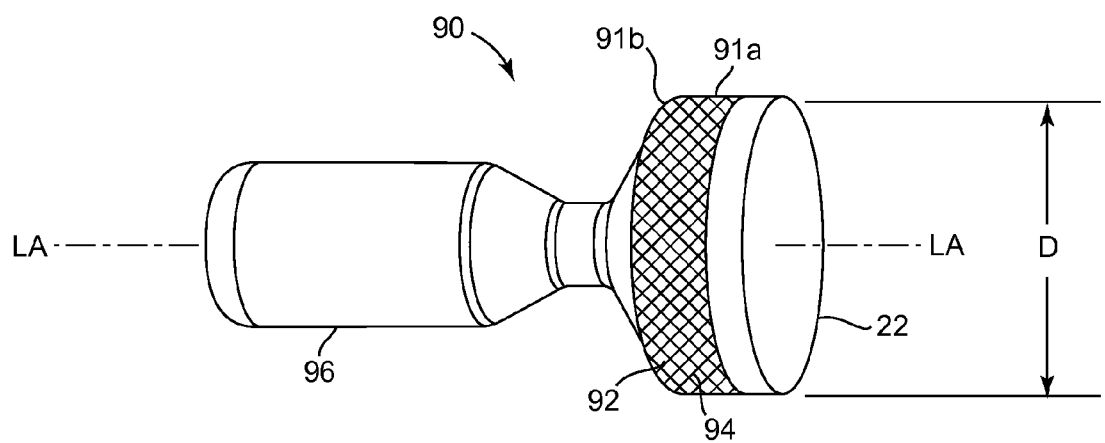
FIG. 10 illustrates an isometric view of the cutting element illustrated in FIG. 9.

FIGS. 9 and 10 illustrate cutting element 90 comprised of cutting blade 22 and abrasive surface 94 on a portion of major diameter 91a and on proximal facing shoulder 91b. When assembled into catheter 2 with cutting element 90 exposed through window 6 in a working or cutting position, cutting element 90 can be advanced distally while rotating about axis LA-LA to cut soft material by means of blade 22 and can be retracted proximally while rotating about axis LA-LA to cut or abrade hard material by means of abrasive surface 94. Cutting element 90 can be used to selectively remove soft material, hard material, or both.

Figure 11:
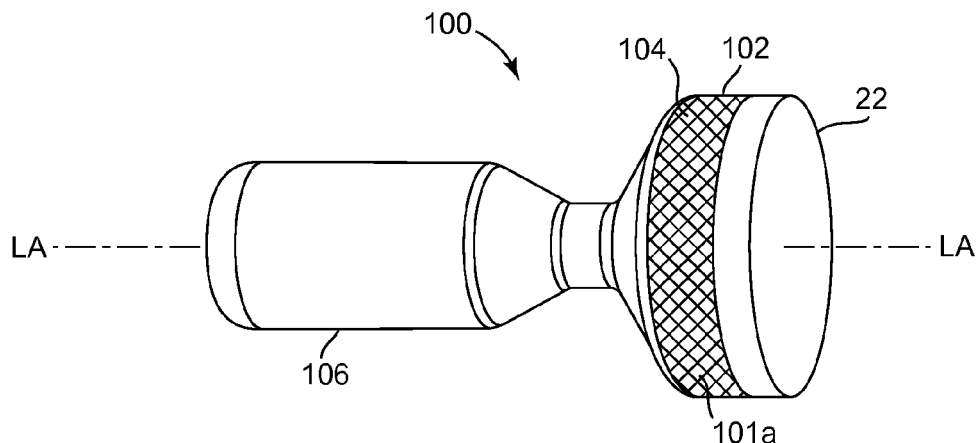
FIG. 11 illustrates an isometric view of a further embodiment of a cutting element suitable for use with the atherectomy catheter illustrated in FIG. 1.
Figure 12:
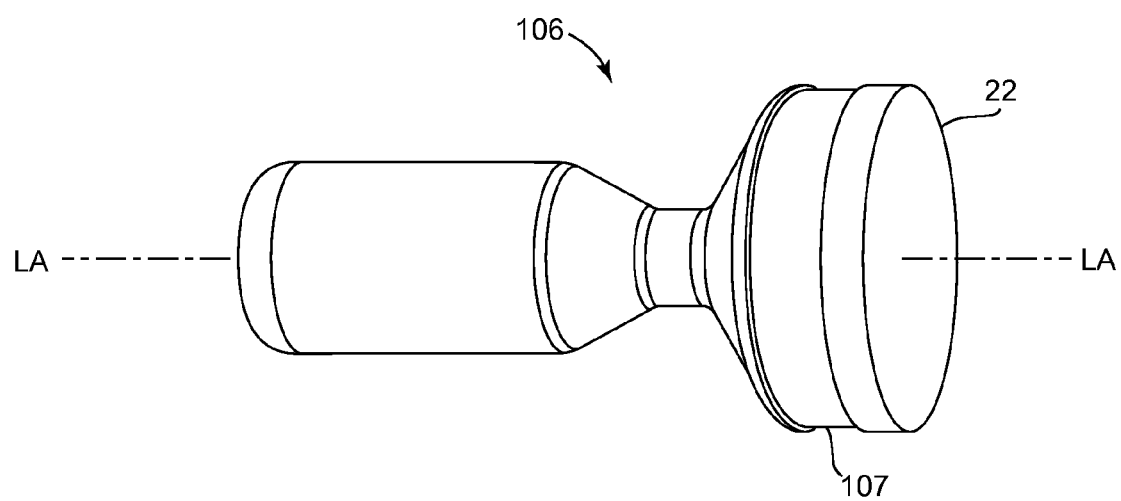
FIG. 12 illustrates an isometric view of one embodiment of a subassembly used to produce the cutting element illustrated in FIG. 11.

FIG. 11 illustrates cutting element 100 comprised of cutting blade 22 and abrasive surface 104 on a portion of major diameter 101a. When assembled into catheter 2 with cutting element 100 exposed through window 6 in a working or cutting position, cutting element 100 can be advanced distally while rotating about axis LA-LA to cut soft material by means of blade 22 and can be retracted proximally while rotating about axis LA-LA to cut or abrade hard material by means of abrasive surface 104. Cutting element 100 can be used to selectively remove soft material, hard material, or both. FIG. 12 illustrates cutter blank 106.

FIG. 13A illustrates cutting element 130 comprised of cutting blade 22 and abrasive surface 134 on all of major diameter 131a and on proximal facing shoulder 131b. When assembled into catheter 2 with cutting element 130 exposed through window 6 in a working or cutting position, cutting element 130 can be advanced distally while rotating about axis LA-LA to cut soft material by means of blade 22 and can be retracted proximally while rotating about axis LA-LA to cut or abrade hard material by means of abrasive surface 134. Cutting element 130 can be used to selectively remove soft material, hard material, or both, and can abrade large amounts of material per pass due to the large surface area covered with abrasive material. FIG. 13B illustrates cutter blank 136.

Figure 14A:
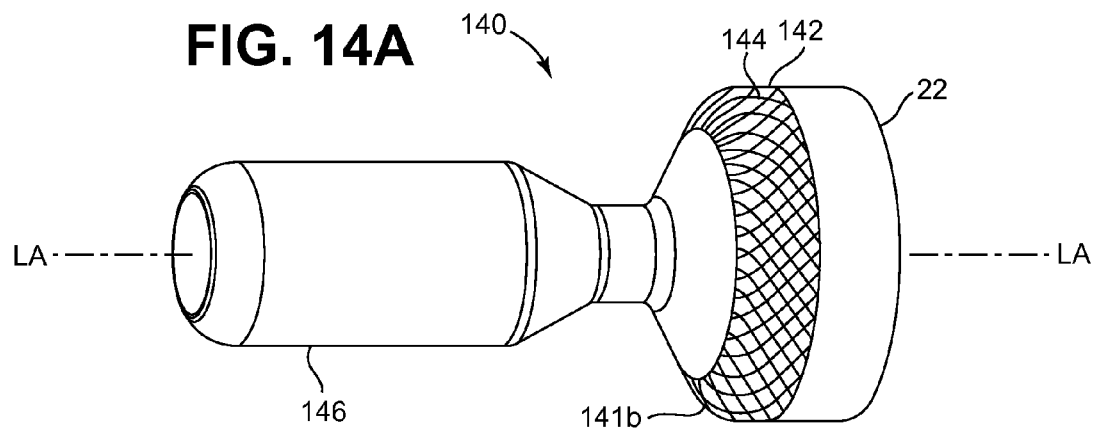
Figure 14B:
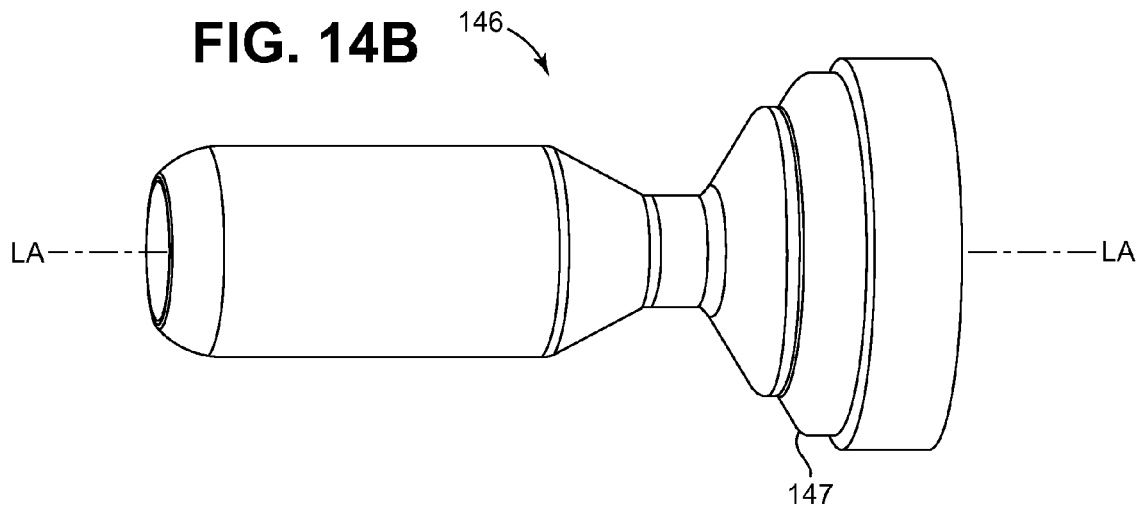

FIG. 14A illustrates cutting element 140 comprised of cutting blade 22 and abrasive surface 144 on proximal facing shoulder 141b. When assembled into catheter 2 with cutting element 140 exposed through window 6 in a working or cutting position, cutting element 140 can be advanced distally while rotating about axis LA-LA to cut soft material by means of blade 22 and can be retracted proximally while rotating about axis LA-LA to cut or abrade hard material by means of abrasive surface 144. Cutting element 140 can be used to selectively remove soft material, hard material, or both, and will abrade less material per pass than cutting element 130 for a given abrasive material grit size, surface speed, and exposure through window 6. FIG. 14B illustrates cutter blank 146.

Figure 15A:
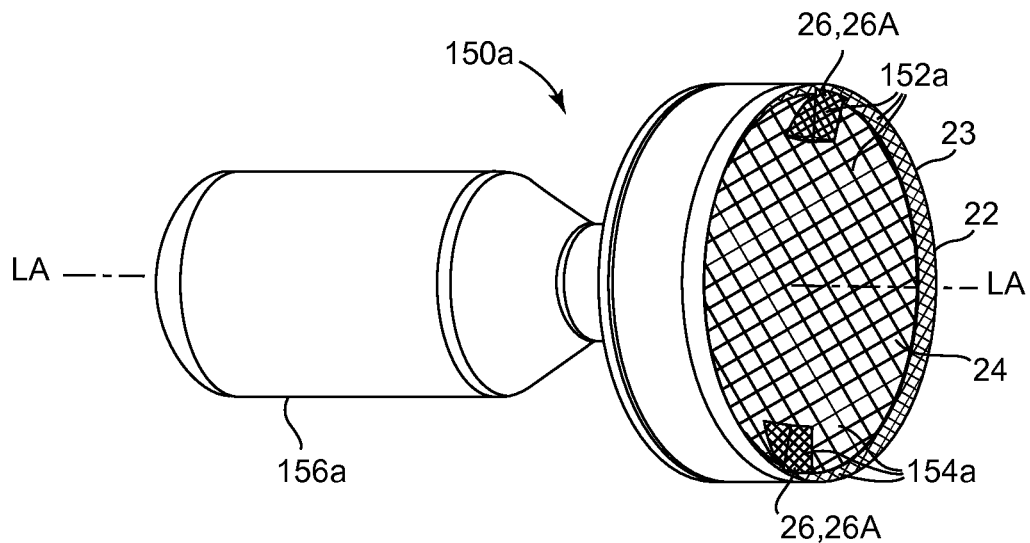

FIG. 15A illustrates cutting element 150a comprised of cutting blade 22, optional raised elements 26, 26A and abrasive surface 154a on cup-shaped surface 24 and optionally on any or all surfaces of raised elements 26, 26A. When assembled into catheter 2 with cutting element 150a exposed through window 6 in a working or cutting position, cutting element 150a can be advanced distally while rotating about axis LA-LA to cut soft material by means of blade 22 and also cut or abrade hard material by means of abrasive surface 154a and (optional) raised elements 26, 26A. Material so cut by cutting element 150a will be directed into tissue chamber 12 by means of cup-shaped surface 24 of cutting element 150a.

Figure 15B:
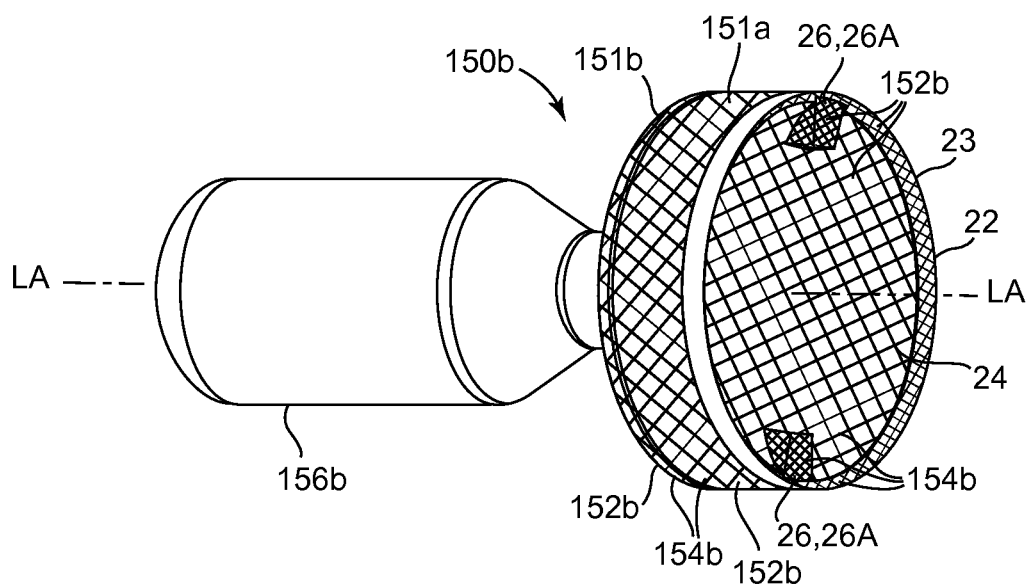

FIG. 15B illustrates cutting element 150b comprised of cutting blade 22, optional raised elements 26, 26A and abrasive surface 154b on cup-shaped surface 24, optionally on any or all surfaces of raised elements 26, 26A, at least a portion of major diameter 151a and on proximal facing shoulder 151b. When assembled into catheter 2 with cutting element 150b exposed through window 6 in a working or cutting position, cutting element 150b can be advanced distally while rotating about axis LA-LA to cut soft material by means of blade 22 and also cut or abrade hard material by means of abrasive surfaces 154b and (optional) raised elements 26, 26A, and can be retracted proximally while rotating about axis LA-LA to cut or abrade hard material by means of abrasive surface 154a on shoulder 151b and major diameter 151a. Material cut by distal advancement of cutting element 150b will be directed into tissue chamber 12 by means of cup-shaped surface 24 of cutting element 150b.

Figure 16A:
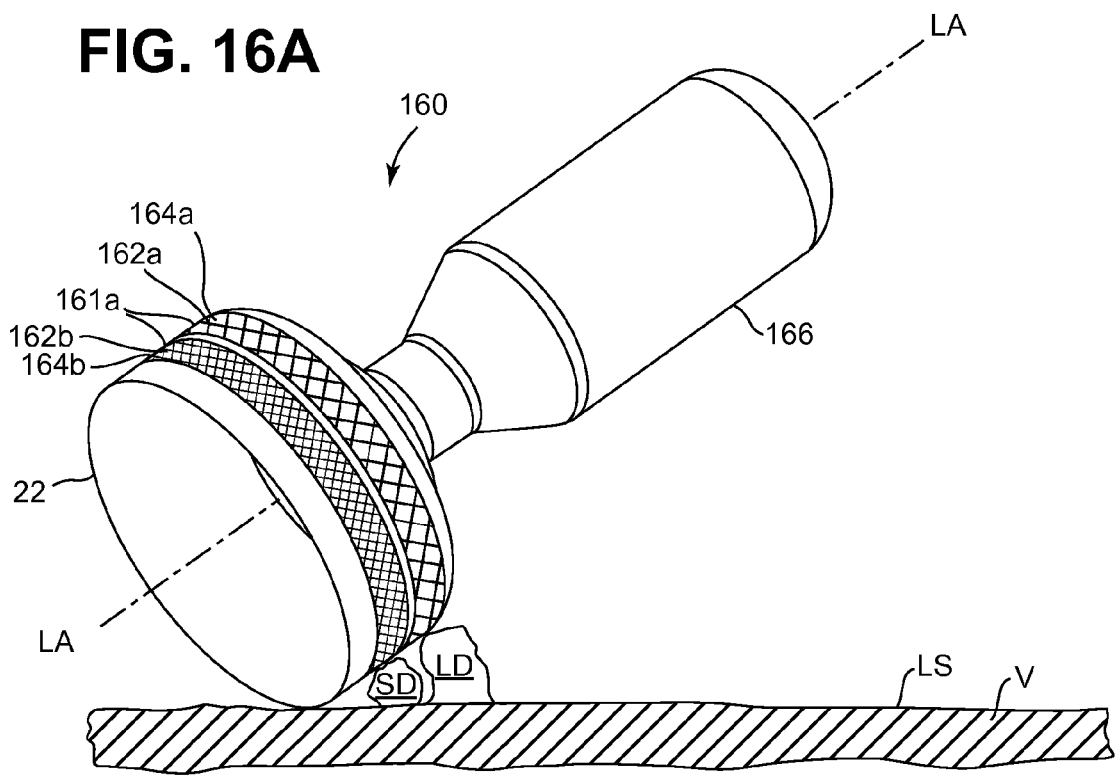
FIGS. 16A and 16B illustrate an isometric view of further embodiments of a cutter and a subassembly suitable for use with the atherectomy catheter illustrated in FIG. 1.
Figure 16B:
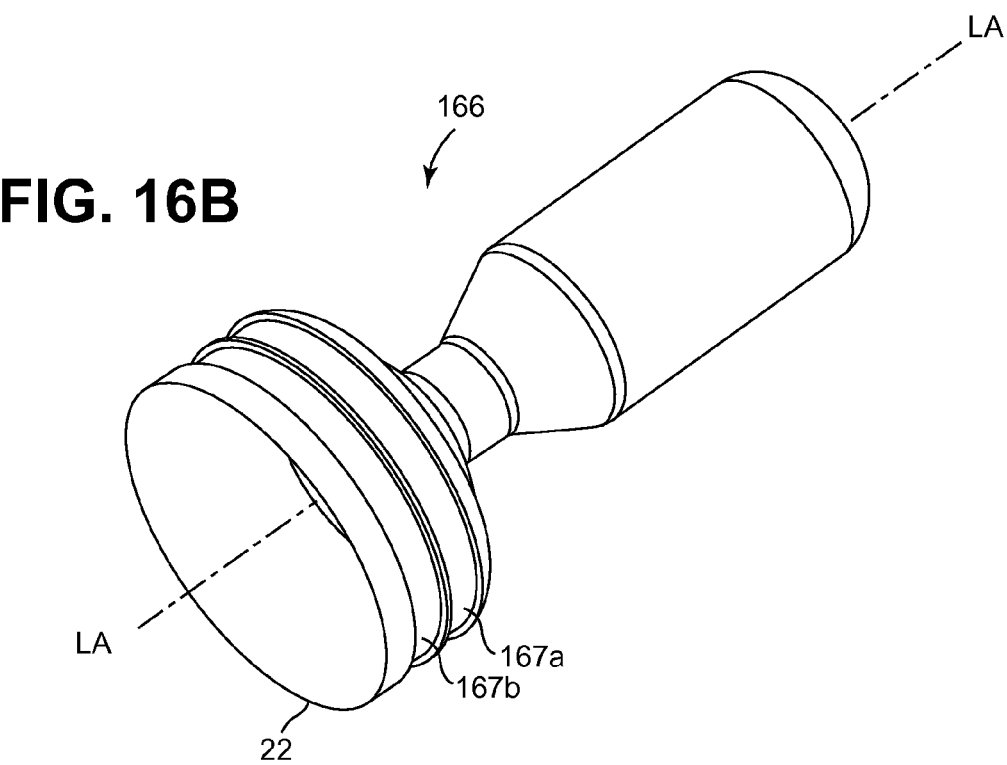

FIG. 16A illustrates cutting element 160 comprised of cutting blade 22 and abrasive surfaces 164a, 164b on a portion of major diameter 161a. When assembled into catheter 2 with cutting element 160 exposed through window 6 in a working or cutting position, cutting element 160 can be advanced distally while rotating about axis LA-LA to cut soft material by means of blade 22 and can be retracted proximally while rotating about axis LA-LA to cut or abrade hard material by means of abrasive surfaces 164a, 164b. In one embodiment abrasive surface 164a is more aggressive than abrasive surface 164b, and will quickly abrade large material deposits LD that extend a large distance from the luminal surface LS of a vessel V, while abrasive surface 164b will slowly abrade small material deposits SD that extend a short distance from the luminal surface LS of a vessel V. Also, in this embodiment, abrasive surface 164b will cause less trauma to luminal surface LS of vessel V than abrasive surface 164a because abrasive surface 164b is less aggressive than abrasive surface 164a. Further, in some embodiments, abrasive surface 164b may be used to polish the luminal surface(s) of deposits in the vessel. FIG. 16B illustrates cutter blank 166.

In some embodiments cutting element 160 may be comprised of more than two surfaces of different abrasive characteristics on major diameter 161a. For example, cutting element 160 may be comprised of 3, 4, 5, 6, or more surfaces of different abrasive characteristics. In one embodiment cutting element 160 is comprised of an abrasive surface that continuously changes from a less aggressive surface to a more aggressive surface on major diameter 161a. In some embodiments the continuously changing abrasive surface is least aggressive at the surface's distal most extent, or most aggressive at the surface's distal most extent.

In another embodiment, catheters 2 comprised of cutting elements 90, 100, 130, 140, 150a, 150b, 160 having both cutting blades and abrasive surfaces may be further comprised of cutter driver 5 capable of rotating the cutting element at two or more speeds. In one embodiment a cutter driver 5 is contemplated that rotates the cutting element at a first speed when cutting with cutting blade 22 and rotates the cutting element at a second speed when abrading with abrasive surface 92, 102, 102', 132, 142, 152a, 152b, 162a, 162b. In some embodiments the first speed is chosen such that cutter surface speed is effective for cutting soft material and the second speed is chosen such that abrasive surface speed is effective for quickly abrading hard material. In other embodiments cutter driver 5 rotates cutting element 90, 100, 130, 140, 150a, 150b, 160 at variable speeds. Cutting element first and second speeds are contemplated to be in the range of 1,000 to 160,000 RPM. In one embodiment, cutting element first and second speeds are 8,000 RPM. In other embodiments cutting element first and second speeds are 1,000 RPM, 2,000 RPM, 4,000 RPM, 16,000 RPM, 32,000 RPM, 64,000 RPM, 80,000 RPM or 120,000 RPM. In some embodiments, cutting element second speed is contemplated to be in the range of 1,000 to 100,000 RPM greater than cutting element first speed. In one embodiment, cutting element second speed is 50,000 RPM greater than cutting element first speed. In other embodiments cutting element second speed is 5,000 RPM, 10,000 RPM, 20,000

RPM, 40,000 RPM or 75,000 RPM greater than cutting element first speed. In still further embodiments cutting element surface speed against the vessel wall material is contemplated to be in the range of 50 to 4,150 surface feet per minute (SFM). In one embodiment, cutting element surface speed is 1,500 SFM. In other embodiments cutting element surface speed is 100 SFM, 200 SFM, 800 SFM, 2,000 SFM or 3,000 SFM. In other embodiments cutting element surface speeds at cutting element second speed (RPM) are contemplated to be in the range of 100 to 3,000 SFM greater than cutting element surface speed at cutting element first speed (RPM). In one embodiment, cutting element second surface speed is 2,000 SFM greater than cutting element first surface speed. In other embodiments cutting element second surface speed is 200 SFM, 500 SFM, 1,000 SFM or 2,500 SFM greater than cutting element first surface speed. Cutting element variable speed ranges, both RPM and SFM, are contemplated to vary within the same ranges as cutting element first and second speeds.

Cutter drivers 5 capable of rotating cutting element 90, 100, 130, 140, 150a, 150b, 160 at a first speed and at a second speed may be comprised of a two position microswitch that electrically connects one battery to motor 11 causing rotation of motor 11 at a first speed and that electrically connects two batteries to motor 11 causing rotation of motor 11 at a second speed, or other means. Cutter drivers 5 capable of rotating cutting element 90, 100, 130, 140, 150a, 150b, 160 at a variable speed may be comprised of a variable resistance microswitch that electrically connects a variable resistance between battery and motor 11 causing variable speed rotation of motor 11, or other means.

Exemplary methods of using an atherectomy catheter comprised of cutting elements having both cutting blades and abrasive surfaces to cut and remove material from a body of a patient are now described.

Figure 18A:
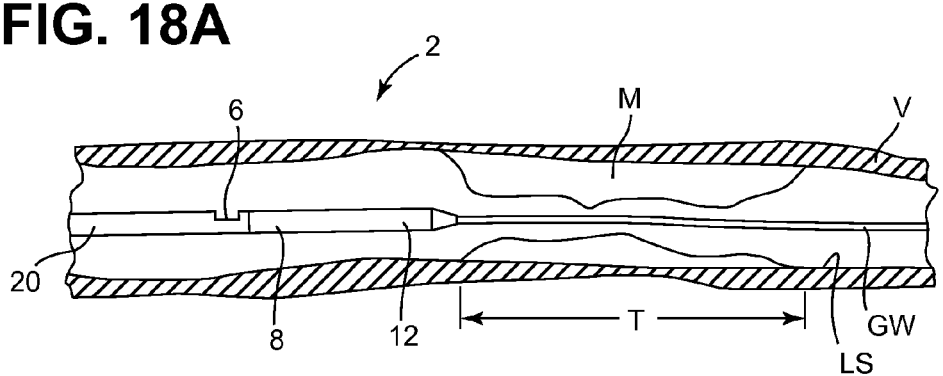
FIGS. 18A, 18B and 18C illustrate schematic views of methods of using catheters having embodiments of cutting elements in a human body.

Using techniques known in the art, a guidewire GW is percutaneously inserted into a patient's body and advanced to a region of interest in a patient's blood vessel V. Using imaging techniques such as fluoroscopy a diseased portion of the vessel is identified and an atherectomy catheter (such as catheter 2) comprised of a cutting element CE, for example cutting element 90, 100, 130, 140, 150b, 160, having appropriate characteristics for treatment site T is chosen. With reference to FIG. 18A, catheter 2 is advanced over the guidewire to the treatment site with the cutting element in a stored position. Using imaging techniques such as fluoroscopy the cutting element is positioned at a desired location relative to (in some methods proximal to) the treatment site.

Figure 18B:
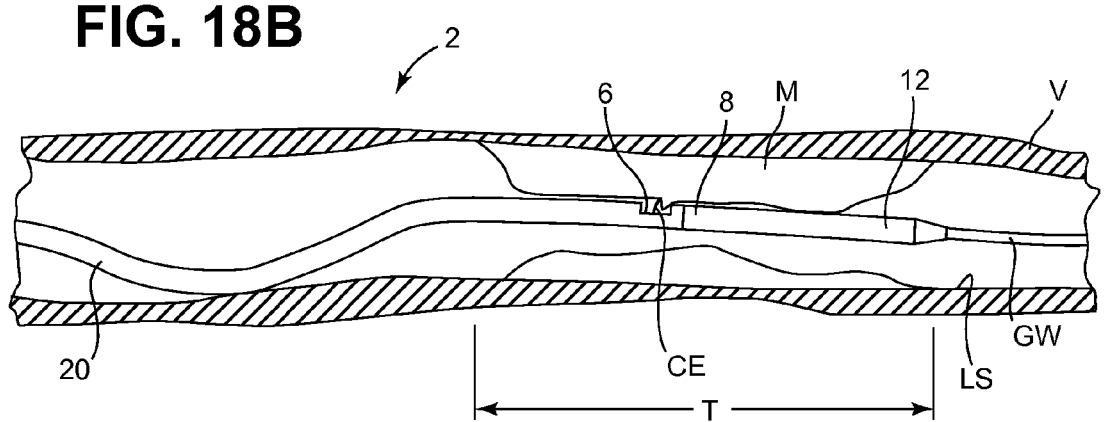
Figure 18C:
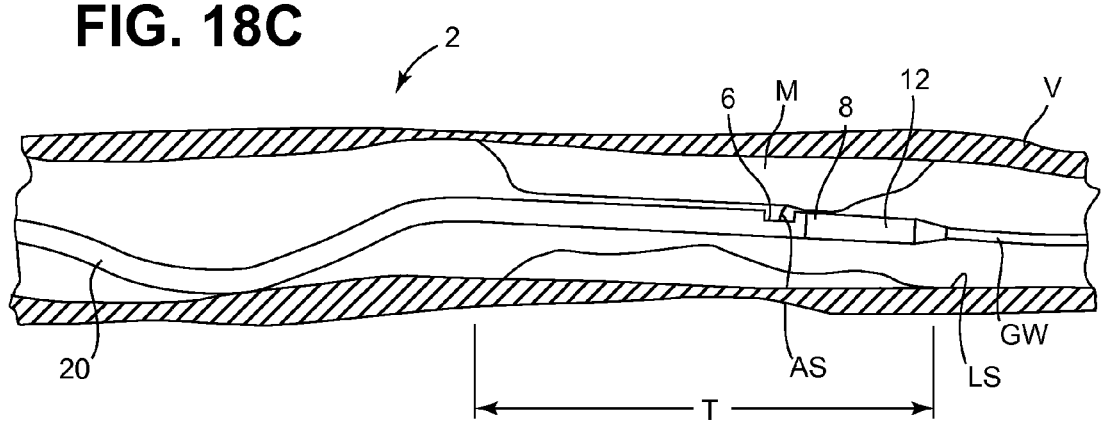

Catheter shaft 20 is held stationary, the cutting element CE is manipulated into a cutting position (i.e. exposed through window 6) and cutting element rotation is activated using lever 13. Catheter shaft 20 is advanced distally causing cutter blade 22 to cut material M from luminal surface LS of vessel V. Cup shaped surface 24 directs cut fragments of material M through thru window 6 into collection chamber 12 (FIG. 18B). Catheter shaft 20 is retracted proximally and abrasive surface AS, for example abrasive surface 92, 102, 102', 132, 142, 152a, 152b, 162a, 162b, abrades material M from luminal surface LS of vessel V (FIG. 18C). Rotation of the cutting element is stopped, the cutting element is returned to the storage position and catheter 2 is withdrawn from the treatment site T.

In some methods the cutting element is rotated at a first speed when cutting material M from luminal surface LS of vessel V and the cutting element is rotated at a second speed when abrading material M from luminal surface LS of vessel V. In some methods the second speed is greater than the first speed.

In another method guidewire GW is percutaneously inserted into a patient's body and advanced to a region of interest in a patient's blood vessel V. Using imaging techniques such as fluoroscopy a diseased portion of the vessel is identified and an atherectomy catheter (such as catheter 2) comprised of a cutting element CE, for example cutting element 150b having appropriate characteristics for treatment site T is chosen. With reference to FIG. 18A, catheter 2 is advanced over the guidewire to the treatment site with the cutting element in a stored position. Using imaging techniques such as fluoroscopy the cutting element is positioned at a desired location relative to (in some methods proximal to) the treatment site.

Catheter shaft 20 is held stationary, the cutting element is manipulated into a cutting position (i.e. exposed through window 6) and cutting element rotation is activated using lever 13. Catheter shaft 20 is advanced distally causing cutter blade 22 to cut and abrasive surface AS to abrade material M from luminal surface LS of vessel V. Cup shaped surface 24 directs cut and abraded fragments of material M through thru window 6 into collection chamber 12 (FIG. 18B). Catheter shaft 20 is retracted proximally and abrasive surface AS, for example abrasive surface 152b, abrades material M from luminal surface LS of vessel V (FIG. 18C). Rotation of the cutting element is stopped, the cutting element is returned to the storage position and catheter 2 is withdrawn from the treatment site T.

In some methods the cutting element is rotated at a first speed when cutting material M from luminal surface LS of vessel V and the cutting element is rotated at a second speed when abrading material M from luminal surface LS of vessel V. In some methods the second speed is greater than the first speed.

In yet another method guidewire GW is percutaneously inserted into a patient's body and advanced to a region of interest in a patient's blood vessel V. Using imaging techniques such as fluoroscopy a diseased portion of the vessel is identified and an atherectomy catheter (such as catheter 2) comprised of a cutting element CE, for example cutting element 150a, having appropriate characteristics for the treatment site T is chosen. With reference to FIG. 18A, catheter 2 is advanced over the guidewire to the treatment site with the cutting element in a stored position. Using imaging techniques such as fluoroscopy the cutting element is positioned at a desired location relative to (in some methods proximal to) the treatment site.

Catheter shaft 20 is held stationary, the cutting element is manipulated into a cutting position (i.e. exposed through window 6) and cutting element rotation is activated using lever 13. Catheter shaft 20 is advanced distally causing cutter blade 22 to cut and abrasive surface AS to abrade material M from luminal surface LS of vessel V. Cup shaped surface 24 directs cut and abraded fragments of material M through thru window 6 into collection chamber 12 (FIG. 18B). Rotation of the cutting element is stopped, the cutting element is returned to the storage position and catheter 2 is withdrawn from the treatment site T.

In some methods the cutting element is rotated at a first speed when cutting material M from luminal surface LS of vessel V and the cutting element is rotated at a second speed when abrading material M from luminal surface LS of vessel V. In some methods the second speed is greater than the first speed.

In addition to use in blood vessels the invention is envisioned to be useful for removal of blockages in other blood flow lumens such as natural or artificial grafts, stent-grafts, anastomotic sites, fistulae, or other blood flow lumens.

The present invention has been described in connection with preferred embodiments but may, of course, be practiced while departing from the above described embodiments. For example, three or more raised elements may be provided or cutting edge may be serrated without departing from numerous aspects of the present invention.

The above description and the drawings are provided for the purpose of describing embodiments of the invention and are not intended to limit the scope of the invention in any way. It will be apparent to those skilled in the art that various modifications and variations can be made without departing from the spirit or scope of the invention. Thus, it is intended that the present invention cover the modifications and variations of this invention provided they come within the scope of the appended claims and their equivalents. Further, while choices for materials and configurations may have been described above with respect to certain embodiments, one of ordinary skill in the art will understand that the materials and configurations described are applicable across the embodiments.

What is claimed is:

1. An atherectomy catheter, comprising:
   a body having opposite proximal and distal ends and a longitudinal axis, the body defining a lumen extending longitudinally therein and an opening in communication with the lumen;
   a rotatable shaft extending longitudinally within the lumen and being rotatable relative to the body; and
   a cutting element adjacent the opening having opposite proximal and distal ends, a length extending between the proximal and distal ends, and an outer, major diameter, the cutting element being coupled to the rotatable shaft for rotating the cutting element relative to the body about a longitudinal axis of the cutting element, the cutting element having a cutting edge configured for cutting tissue as the cutting element rotates and an abrasive surface spaced apart from the cutting edge on at least a longitudinal portion of an outer, major diameter surface of the cutting element configured for abrading tissue as the cutting element rotates,
   wherein the cutting element has a working position in which the cutting edge and the abrasive surface of the cutting element are exposed through the opening in the body to engage tissue outside the body of the atherectomy.

2. The catheter of claim 1, wherein the cutting edge is a radially outer edge of the cutting element.

3. The catheter of claim 1, wherein the cutting element is movable between a stored position and the working position relative to the opening.

4. The catheter of claim 3, wherein the cutting element is moved between the stored position and the working position by sliding the cutting element against a cam surface.

5. The catheter of claim 4, wherein a distal portion of the atherectomy catheter relative to a proximal portion is deflected by sliding the cutting element against the cam surface.

6. The catheter of claim 1, wherein the abrasive surface is flush in relation to adjacent non-abrasive cutting element surfaces.

7. The catheter of claim 1, wherein the outer, major diameter of the cutting element is in the range of 0.030 to 0.100" (0.076 to 0.25 cm).

8. The catheter of claim 1, wherein the outer, major diameter of the cutting element is 0.061" (0.15 cm).

9. The catheter of claim 1, wherein the abrasive surface comprises one contiguous abrasive surface.

10. The catheter of claim 1, wherein the abrasive surface is comprised of abrasive material that has been attached to the cutting element.

11. The catheter of claim 10, wherein the abrasive material comprises diamond plate.

12. The catheter of claim 10, wherein the abrasive material has a particle size of 10 to 800 microns.

13. The catheter of claim 1, wherein the abrasive surface has been produced without attaching abrasive materials to the cutting element.

14. The catheter of claim 13, wherein the abrasive surface has been produced by knurling, grit blasting, etching, or laser ablation.

15. The catheter of claim 1, wherein the abrasive surface is on a proximal facing shoulder surface of the cutting element.

16. A method of removing material from a body lumen, the method comprising:
    providing an atherectomy catheter, the atherectomy catheter comprising:
      a body having opposite proximal and distal ends and a longitudinal axis, the body defining a lumen extending longitudinally therein and an opening in communication with the lumen;
      a rotatable shaft extending longitudinally within the lumen and being rotatable relative to the body; and
      a cutting element adjacent the opening having opposite proximal and distal ends, a length extending between the proximal and distal ends, and an outer, major diameter, the cutting element being coupled to the rotatable shaft for rotating the cutting element relative to the body about a longitudinal axis of the cutting element, the cutting element having a cutting edge configured for cutting tissue as the cutting element rotates and an abrasive surface spaced apart from the cutting edge on at least a longitudinal portion of an outer, major diameter surface of the cutting element configured for abrading tissue as the cutting element rotates, wherein the cutting element has a working position in which the cutting edge and the abrasive surface of the cutting element are exposed through the opening in the body to engage tissue outside the body of the atherectomy catheter;
    placing the atherectomy catheter in the body lumen; and
    moving the atherectomy catheter in the body lumen, with the cutting element in the working position, to contact the cutting element with the material in the body lumen.

17. The method of claim 16, wherein the atherectomy catheter is moved in a distal direction to contact the cutting edge with the material in the body lumen.

18. The method of claim 17, wherein the atherectomy catheter is moved in a proximal direction to contact the abrasive surface with the material in the body lumen.

19. The method of claim 18, wherein the abrasive surface is on a proximal facing shoulder surface of the cutting element.

20. The method of claim 16, wherein the atherectomy catheter is placed in the body lumen with the cutting element in a stored position and the atherectomy catheter is moved to contact the material with the cutting element in the working position.

* * * * *